US008242162B2

(12) United States Patent
Meador et al.

(10) Patent No.: US 8,242,162 B2
(45) Date of Patent: Aug. 14, 2012

(54) FLUORESCENT AROMATIC SENSORS AND THEIR METHODS OF USE

(75) Inventors: Michael A. Meador, Strongsville, OH (US); Daniel S. Tyson, Amherst, OH (US); Ulvi F. Ilan, Istanbul (TR)

(73) Assignees: Ohio Aerospace Institute, Cleveland, OH (US); The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 949 days.

(21) Appl. No.: 11/956,848

(22) Filed: Dec. 14, 2007

(65) Prior Publication Data

US 2008/0242870 A1 Oct. 2, 2008

Related U.S. Application Data

(60) Provisional application No. 60/875,091, filed on Dec. 15, 2006.

(51) Int. Cl.
*A61K 31/403* (2006.01)
*C07D 209/56* (2006.01)

(52) U.S. Cl. .......................... 514/410; 548/418; 548/426

(58) Field of Classification Search .................... 548/418
See application file for complete search history.

(56) References Cited

U.S. PATENT DOCUMENTS

| 6,916,660 | B2 | 7/2005 | Wang et al. |
| 2005/0148086 | A1 | 7/2005 | Hamachi |
| 2005/0186555 | A1 | 8/2005 | Lippard et al. |
| 2006/0240565 | A1 | 10/2006 | Tang et al. |

OTHER PUBLICATIONS

Ilhan, et al.; Twisted, Z-Shaped Perylene Bisimide; J. Am. Chem. Soc. 2006, 128, 702-703.
Ilhan, et al., Phenacenes from Diels-Alder Trapping of Photogenerated o-Xylylenols: Phenanthrenes and Benzo [e] pyrene Bisimide; Organic Letters 2006, vol. 8, No. 4, p. 577-580.
Ilhan, et al., Synthesis and Chemosensory Behavior of Anthracene Bisimide Derivatives, Chem. Mater. 2004, 16, p. 2978-2980.
Basabe-Desmonts, et al., Design of Flourescent Materials for Chemical Sensing, Chem. Soc. Rev., 2007, 36, p. 993-1017.
Wintgens, et al., Spectroscopic properties of aromatic dicarboximides Part 3: Substituent Effect on the Photophysical Properties of N-Phenyl-2,3-Naphthalimides; Journal of Photochemistry and Photobiology A: Chemistry 93, 1996, p. 109-117.
Cao, et al., Matrix Screening of Substituted N-Aryl-1,8-Naphthalimides Reveals New Dual Fluorescent Dyes and Unusually Bright Pyridine Derivatives; J. Org. Chem, 2005, 70, p. 4929-4934.
Zhang et al., Fluorescent Detection of Chemical Warfare Agents: Functional Group Specific Ratiometric Chemosensors; J. Am. Chem. Soc., 2003, 125, p. 3420-3421.
Zang et al., A Single-Molecule Probe Based on Intramolecular Electron Transfer; J. Am. Chem. Soc., 2002, 124, p. 10640-10641.
Langhals, Heinz, et al., Persistent Fluorescence of Perylene Dyes by Steric inhibition of Aggregation; Tetrahedron 56, 2000, p. 5435-5441.
James et al., Novel Saccharide-Photoinduced Electron Transfer Sensors Based on the Interaction of Boronic Acid and Amine; J. Am. Chem. Soc., 1995, 117, 8982-8987.
Hoeben, et al., About Supramolecular Assemblies of Pi-Conjugated Systems; Chem. Rev., 2005, 105, p. 1491-1546.
Marinez-Manez, et al., Fluorogenic and Chromogenic Chemosensors and Reagents for Anions; Chem. Rev., 2003, 103, p. 4419-4476.
Wurthner, et al., Preparation and Characterization of Regioisomerically Pure 1, 7-Disubstituted Perylene Bisimide Dyes; J. Org. Chem., 2004, 69, p. 7933-7939.
Williams, et al., Relative Fluorescence Quantum Yields Using a Computer-controlled Luminescence Spectrometer; Analyst; Sep. 1983, 108, p. 1067-1071.
McBride, et al., Multiplexed Liquid Arrays for Simultaneous Detection of Simulants of Biological Warfare Agents; Anal. Chem., 2003, 75, 1924-1930.

*Primary Examiner* — Shawquia Young
(74) *Attorney, Agent, or Firm* — Pearne & Gordon LLP

(57) ABSTRACT

Aromatic molecules that can be used as sensors are described. The aromatic sensors include a polycyclic aromatic hydrocarbon core with a five-membered imide rings fused to the core and at least two pendant aryl groups. The aromatic sensor molecules can detect target analytes or molecular strain as a result of changes in their fluorescence, in many cases with on-off behavior. Aromatic molecules that fluoresce at various frequencies can be prepared by altering the structure of the aromatic core or the substituents attached to it. The aromatic molecules can be used as sensors for various applications such as, for example, the detection of dangerous chemicals, biomedical diagnosis, and the detection of damage or strain in composite materials. Methods of preparing aromatic sensor molecules are also described.

14 Claims, 11 Drawing Sheets

LINEAR BISIMIDE
R = GENERIC GROUP

Z-SHAPED BISIMIDE (1)
R = n-$C_8H_{17}$

FLUORESCENT AROMATIC SENSORS AND THEIR METHODS OF USE

CONTINUING APPLICATION DATA

This application claims the benefit of U.S. Provisional Application Ser. No. 60/875,091, filed Dec. 15, 2006, which is incorporated by reference herein.

GOVERNMENT FUNDING

The present invention was made with government support under Grant No. NCC3-1089, awarded by the NASA Glenn Research Center. The Government may have certain rights in this invention.

BACKGROUND

Fluorescence based methods for the detection of chemical and biological species area have attracted considerable attention because of their high sensitivity and ease of use and because instrumentation for these methods can be incorporated into small, compact devices that have low power requirements. These techniques frequently employ a fluorescent dye that interacts with a target analyte or family of analytes to produce a change in the fluorescence properties of the dye. These dye-analyte interactions may be signaled by changes in photoinduced properties such as absorption, emission intensity, or wavelength, and luminescence lifetime. Quenching of photoluminescence intensity is of particular interest as sensitivity is inherently enhanced due to a distinct contrast between signaling events (i.e., luminescent and non-luminescent states). See Martinez-Manez, R.; Sancenon, F., Chem. Rev. 203, 103, 4419. Researchers have utilized photo-induced electron transfer (PET), energy transfer, and other mechanisms to produce "on/off" sensors based on aromatic and polycyclic aromatic hydrocarbons, aromatic heterocycles, and transition metal complexes. See McQuade et al., Chem. Rev. 2000, 100, 2537 and Granda-Valdes et al., Quim. Anal. 2000, 19, 38.

A number of fluorescent sensor compounds have been developed for detecting saccharides. For example, U.S. Pat. No. 6,916,660 describes fluorescent anthracene molecules bearing boronic acids that selectively bind and detect various monosaccharides and polysaccharides. In addition, a number of metal-detecting fluorescent sensor compounds have been developed. For example, U.S. patent application Ser. No. 11/039,396 describes naphthofluorescein-based ligands that bind metal ions such as $Hg^{2+}$ and $Na^+$ with a concomitant change in fluorescence. The sensing of chemical warfare agents using chemosensors has also gained increasing attention. See McBride et al., Anal. Chem. 2003, 75, 1924. For example, Swager et al. reported functional group specific chemosensors that incorporated a transduction/cyclization process specific to highly reactive organophosphates and related compounds. See Zhang, S.-W.; Swager, T. M. J. Am. Chem. Soc. 2003, 125, 3420. However, there remains a need for chemical sensors that may be functionalized to respond to generic or specific target molecules.

Aromatic diimides have been employed extensively as fluorescent sensor dyes. Hoeben, et al., J. Chem. Rev. 2005, 105, 1491. An important requirement for the use of diimide linking groups in these systems is that the aromatic nucleus must be polarizable to allow facile charge transfer between donor and acceptor groups. With a very few exceptions, these efforts have been reported for naphthalene and perylene diimides due, for the most part that these systems can be readily prepared from commercially available naphthalene and perylene dianhydride. Accounts regarding anthracence-based imides, however, are limited due to synthetic challenges and limited solubility of anthracene-based imides. A versatile approach to preparing anthracene diimides would be highly desirable, enabling further investigations of their properties and potential application as sensor molecules.

Another type of aromatic diimides are perylene diimides. For example, Zang et al. have demonstrated a perylene diimide that can be used as an on-off single molecule fluorescent sensor. See Zang et al., J. Am. Chem. Soc. 2002, 124, 10640-1. A number of linear perylene diimides (FIG. 10) have been prepared from commercially available perylene anhydride or dianhydride and a wide array of amines via conventional imidization chemistry. Alkyl amines or amine terminated polyethylene glycols have been used to enhance solubility and/or impart liquid crystallinity. Approaches have also been reported to asymmetrically substituted diimides containing both a solubilizing group and a unit, e.g. an electron donor or acceptor, to endow a specific function to the perylene. See Langhals et al., Tetrahedron 2000, 56, 5435-41. Significant attention has also been given to attaching pendant groups directly to the perylene core, which can dramatically alter excited state properties. See Würthner. et al., J. Org. Chem. 2004, 69, 7933-9. However, the current synthetic methods for adding pendant substituents to perylene are limited both in terms of the types of substituents that can be attached as well as where they can be placed on the perylene. Greater flexibility in the types and placement of these substituents would enable the design of new perylenes with a wider range of spectral and sensory properties.

Accordingly, there remains a need in the art for fluorescent compounds that can be designed to sense a variety of different target molecules and fluoresce at a variety of different wavelengths. In addition, there remains a need for fluorescent compounds that exhibit high quantum yields and stability. Furthermore, there remains a need to develop procedures for readily synthesizing such fluorescent compounds.

SUMMARY

In one aspect, the present invention provides an aromatic sensor molecule that includes a polycyclic aromatic hydrocarbon core including a five-membered imide ring fused to the core bearing a sensor group on a nitrogen atom of the imide ring, and at least two pendant aryl groups on the core, wherein the sensor groups quench or modulate the fluorescence of the polycyclic aromatic hydrocarbon core unless the sensor groups interact with a target analyte. In one embodiment of the sensor molecule, the polycyclic aromatic hydrocarbon is selected from the group consisting of anthracene, phenanthrene, perylene, and benzo[e]pyrene. In a further embodiment, the sensor groups are selected from the group consisting of aryl-crown ethers, aryl amines, porphyrins, and phenyl boronic acid.

In another embodiment, the aromatic sensor molecule is a diimide that includes two-five membered imide rings fused to the core. For example, the aromatic sensor molecule may have a structure according to Formula I:

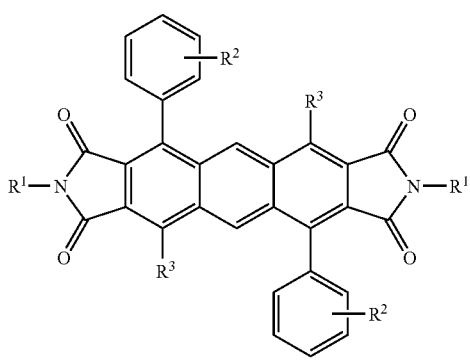

wherein R¹ is selected from the group consisting of aryl-crown ethers, aryl amines, porphyrins, and phenyl boronic acid, R² is selected from the group consisting of hydrogen, alkyl, haloalkyl, halogen, alkoxy, cyano, nitro, amino, alkylamino, carboxyl, and hydroxyl moieties, and R³ is selected from the group consisting of hydrogen or a phenyl group including an R² substituent.

As another example, the aromatic sensor molecule may have a structure according to Formula II:

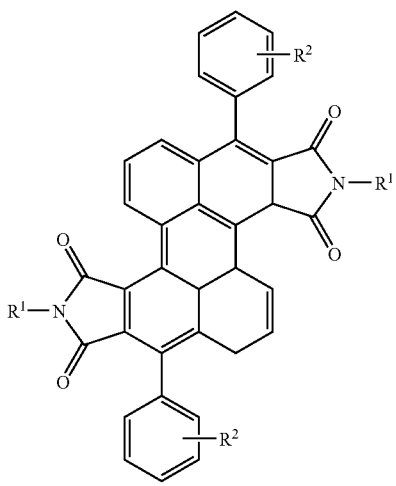

wherein R¹ is selected from the group consisting of aryl-crown ethers, aryl amines, porphyrins, and phenyl boronic acid, and R² is selected from the group consisting of hydrogen, alkyl, haloalkyl, halogen, alkoxy, cyano, nitro, amino, alkylamino, carboxyl, and hydroxyl moieties.

As a further example, the aromatic sensor molecule may have a structure according to Formula III:

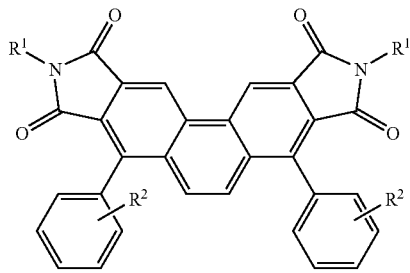

wherein R¹ is selected from the group consisting of aryl-crown ethers, aryl amines, porphyrins, and phenyl boronic acid, and R² is selected from the group consisting of hydrogen, alkyl, haloalkyl, halogen, alkoxy, cyano, nitro, amino, alkylamino, carboxyl, and hydroxyl moieties.

As yet another example, the aromatic sensor molecule may have a structure according to Formula IV:

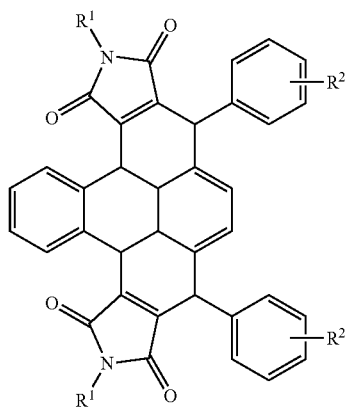

wherein R¹ is selected from the group consisting of aryl-crown ethers, aryl amines, porphyrins, and phenyl boronic acid, and R² is selected from the group consisting of hydrogen, alkyl, haloalkyl, halogen, alkoxy, cyano, nitro, amino, alkylamino, carboxyl, and hydroxyl moieties.

In another embodiment, the pendant aryl groups of the aromatic sensor molecule are attached to a polymer. In a further embodiment, the pendant aryl groups are attached to a nanoparticle. Embodiments of the aromatic sensor molecule may also exhibit peak fluorescence at a wavelength from about 450 to about 800 nanometers. In yet another embodiment, the aromatic sensor molecule is photostable.

In another aspect, the present invention provides a method of detecting a target analyte using an aromatic sensor molecule that includes a polycyclic aromatic hydrocarbon core including a five-membered imide ring fused to the core bearing a sensor group on a nitrogen atom of the imide ring, and at least two pendant aryl groups on the core, wherein the sensor groups quench or modulate the fluorescence of the polycyclic aromatic hydrocarbon core unless the sensor groups interact with a target analyte. In one embodiment, the method may be used to detect a target analyte that is an acid or metal ion. In a further embodiment, the method may be used to detect a target analyte that is a nitroaromatic explosive compound. In yet another embodiment, the method may be used to detect a target analyte that is a chemical warfare agent.

In another aspect, the present invention provides an aromatic sensor molecule with a structure according to Formula II:

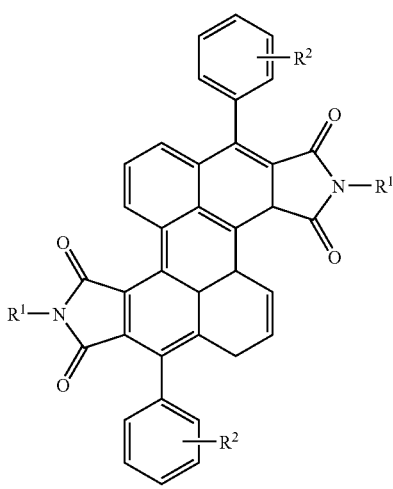

wherein R¹ is selected from the group consisting of alkyl, alkoxy, or alkoxyphenyl, and R² is selected from the group consisting of hydrogen, alkyl, haloalkyl, halogen, alkoxy, cyano, nitro, amino, alkylamino, carboxyl, and hydroxyl moieties. Aromatic sensors of this type may be used in a method of detecting molecular strain.

In a further aspect, the present invention provides a method of preparing an anthracene sensor molecule that includes the step of reacting 1,5-bis(phenyl)anthracene-2,3,6,7-tetracarboxyl bisanhydride with a primary alkyl- or arylamine by refluxing in a suitable organic solvent in the presence of an acid. In one embodiment of this method, the primary alkyl- or arylamine is selected from the group consisting of, 4-tertbutylanaline, 2-(aminomethyl)-18-crown-6,4'-aminobenzo 15-crown-5, triphenyl amine, and 3-aminophenyl boronic acid monohydrate.

The above summary of the present invention is not intended to describe each disclosed embodiment or every implementation of the present invention. The description that follows more particularly exemplifies illustrative embodiments.

DETAILED DESCRIPTION OF ILLUSTRATIVE EMBODIMENTS

Definitions

Figure 1:
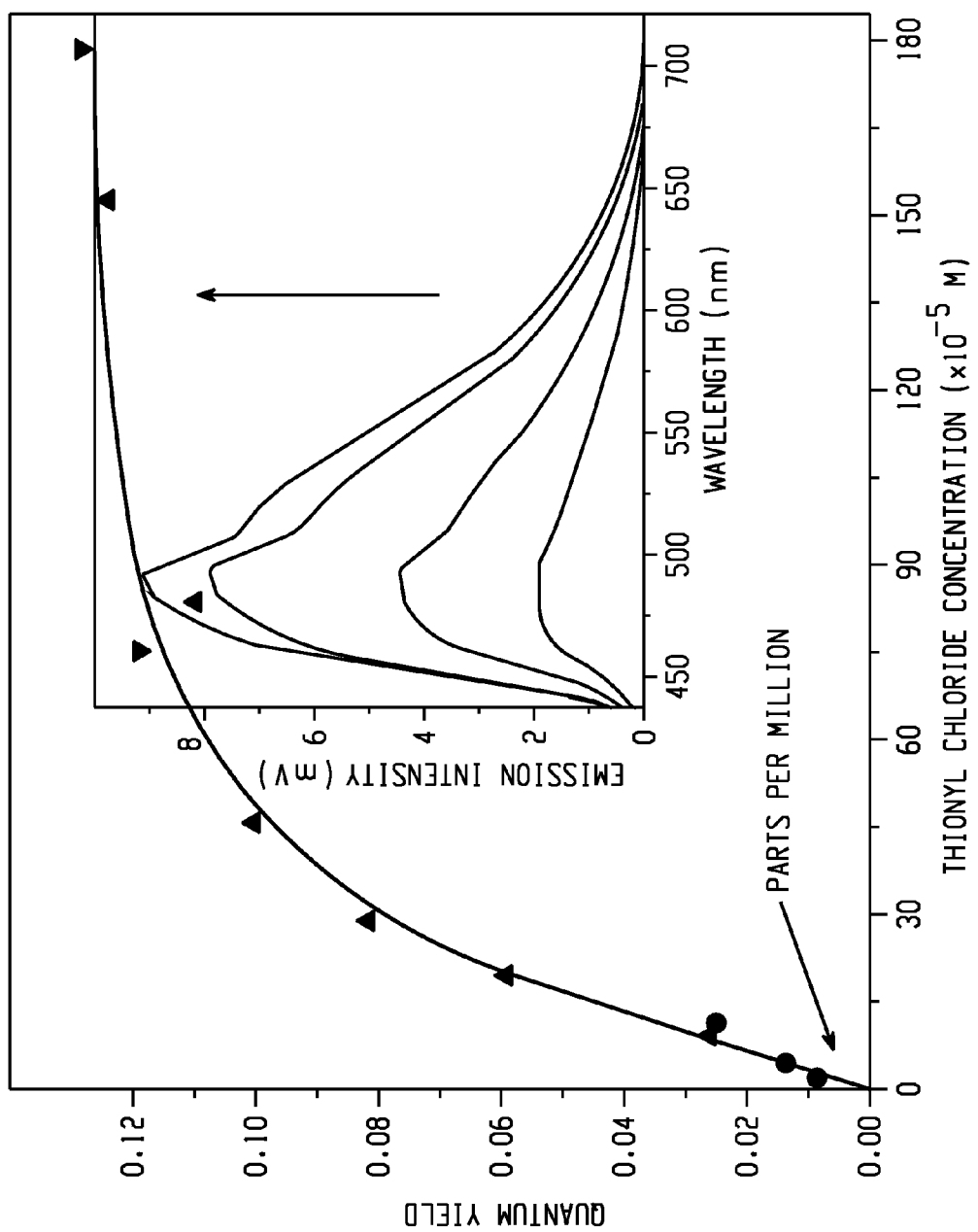
FIG. 1 shows the luminescence titration curve of N,N'-bis (p-aminophenyl)-1,5-bis(p-tetraethyleneglycoloxy)phenyl) anthracene-2,3,6,7,-tetracarboxyl bisimide resulting from additions of thionyl chloride. The complete curve represents three independent experiments with varying initial concentrations of thionyl chloride. The insert represents emission spectra recorded with 425 nm excitation.

Unless otherwise specified, "a," "an," "the," and "at least one" are used interchangeably and mean one or more than one.

The terminology as set forth herein is for description of the embodiments only and should not be construed as limiting of the invention as a whole. As used in the description of the invention and the appended claims, the singular forms "a", "an", and "the" are inclusive of their plural forms, unless contraindicated by the context surrounding such.

The terms "comprising" and variations thereof do not have a limiting meaning where these terms appear in the description and claims.

As used herein, the term "organic group" is used for the purpose of this invention to mean a hydrocarbon group that is classified as an aliphatic group, cyclic group, or combination of aliphatic and cyclic groups (e.g., alkaryl and aralkyl groups). In the context of the present invention, the term "aliphatic group" means a saturated or unsaturated linear or branched hydrocarbon group. This term is used to encompass alkyl, alkenyl, and alkynyl groups, for example.

As used herein, the terms "alkyl", "alkenyl", and the prefix "alk-" are inclusive of straight chain groups and branched chain groups and cyclic groups, e.g., cycloalkyl and cycloalkenyl. Unless otherwise specified, these groups contain from 1 to 20 carbon atoms, with alkenyl groups containing from 2 to 20 carbon atoms. In some embodiments, these groups have a total of at most 10 carbon atoms, at most 8 carbon atoms, at most 6 carbon atoms, or at most 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

The term "heterocyclic" includes cycloalkyl or cycloalkenyl non-aromatic rings or ring systems that contain at least one ring heteroatom (e.g., O, S, N).

Unless otherwise specified, "alkylene" and "alkenylene" are the divalent forms of the "alkyl" and "alkenyl" groups defined above. The terms, "alkylenyl" and "alkenylenyl" are used when "alkylene" and "alkenylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are chloromethyl, trifluoromethyl, and the like. Halogens are elements including chlorine, bromine, fluorine, and iodine.

The term "aryl" as used herein includes monocyclic or polycyclic aromatic hydrocarbons or ring systems. Examples of aryl groups include phenyl, naphthyl, biphenyl, fluorenyl and indenyl. Aryl groups may be substituted or unsubstituted. Aryl groups include aromatic annulenes, fused aryl groups, and heteroaryl groups. Aryl groups are also referred to herein as aryl rings.

Unless otherwise indicated, the term "heteroatom" refers to the atoms O, S, or N.

The term "diimide" refers to molecules including two groups including the —C(O)—NR$_1$—C(O)— functionality. Another term that may be used to describe diimides is the term bisimide. For example, bismaleimide is a diimide.

The term "heteroaryl" includes aromatic rings or ring systems that contain at least one ring heteroatom (e.g., O, S, N). In some embodiments, the term "heteroaryl" includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The terms "arylene" and "heteroarylene" are the divalent forms of the "aryl" and "heteroaryl" groups defined above. The terms "arylenyl" and "heteroarylenyl" are used when "arylene" and "heteroarylene", respectively, are substituted. For example, an alkylarylenyl group comprises an arylene moiety to which an alkyl group is attached.

The term "fused aryl ring" includes fused carbocyclic aromatic rings or ring systems. Examples of fused aryl rings include benzo, naptho, fluoreno, and indeno rings. The term "polycyclic aromatic hydrocarbon" includes fused aryl rings that include three or more aromatic rings. Small polycyclic aromatic hydrocarbons are those that include three to six aromatic rings, whereas large polycyclic aromatic hydrocarbons are those that include more than six aromatic rings.

When a group is present more than once in any formula or scheme described herein, each group (or substituent) is independently selected, whether explicitly stated or not. For example, for the formula —C(O)—NR$_2$ each of the two R groups is independently selected. More specifically, a substituent is an atom or a group of atoms substituted in place of a hydrogen atom on the parent hydrocarbon.

As a means of simplifying the discussion and the recitation of certain terminology used throughout this application, the terms "group" and "moiety" are used to differentiate between chemical species that allow for substitution or that may be substituted and those that, in the particular embodiment of the invention, do not so allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, tert-butyl, and the like.

The term "fluorophore" refers to a chromophore that fluoresces. Such compounds absorb light in the infrared, visible or ultraviolet and emit light (fluoresce) at longer wavelengths. Typically, most organic fluorophores absorb and emit in the visible and/or ultraviolet. Compounds that emit in the infrared or near-infrared are desirable for biological sensor applications in order to mitigate background effects from surrounding biochemical species and because infrared and near-infrared light cause less tissue damage than ultraviolet.

The present invention is directed, in part, to aromatic sensor molecules that include a polycyclic aromatic hydrocarbon core, at least one five-membered imide ring fused to the core that bears a sensor group on the imide nitrogen atom, and at least two pendant bulky groups (e.g., aryl, heteroaryl or bulky alkyl groups) on the core. The aromatic sensor molecules may be represented schematically by the following formula, which notionally illustrates an aromatic sensor molecule:

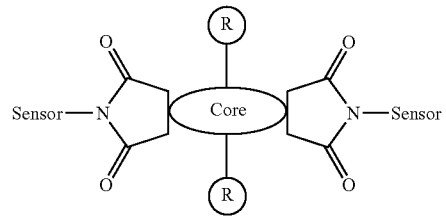

The aromatic sensor molecules thus have four different functional regions. These are the polycyclic aromatic hydrocarbon core, the five-membered imide rings, the pendant bulky groups (R), and the sensor groups, all of which are described in greater detail below. While the aromatic sensor molecule shown above is a diimide sensor molecule, the sensor molecules of invention may include one or more imide rings.

The first of these regions is the polycyclic aromatic hydrocarbon core. The polycyclic aromatic hydrocarbon core comprising a fused aryl ring system that can act as a fluorophore. The aromatic core can comprise any polycyclic aromatic hydrocarbon that provides a fluorescent quantum yield of 0.1 or more. The polycyclic aromatic core can be either a small polycyclic aromatic hydrocarbon or a large polycyclic aromatic hydrocarbon. Examples of small polycyclic aromatic ring systems suitable for use as the aromatic core include anthracene, phenanthrene, perylene, and benzo[e]pyrene. Other suitable aromatic ring systems include chrysene, helicene, tetracene, and triphenylene. Anthracene is a polycyclic aromatic hydrocarbon composed of three benzene rings fused in a linear fashion. Phenanthrene is a polycyclic aromatic hydrocarbon composed of three benzene rings fused to provide a C-shaped structure. Perylene is a polycyclic aromatic hydrocarbon composed of five benzene rings fused together which may be described as two naphthalene molecules connected by a carbon-carbon bond at the 1 and 8 positions on both molecules. Benzo[e]pyrene is another five-ring polycyclic aromatic hydrocarbon, with a configuration known to those skilled in the art. Large polycyclic aromatic hydrocarbons may be preferred for applications in which longer wavelength emission (e.g., about 700 nm) is desired.

Fused to the polycyclic aromatic hydrocarbon core is at least one five-membered imide ring. In some embodiments, the aromatic sensor molecule is a diimide that includes two-five membered imide rings fused to the core. Additional embodiments may thus include two or more imide rings fused to the core. Appropriate substitution at the imide ring nitrogen imparts that capability to sense target analytes and function as an aromatic sensor molecule. In some embodiments, the imide rings provide the capacity for the aromatic sensors molecules to operate as on-off sensors. Positioning of the five-membered imide rings on the aromatic core may be varied to provide aromatic sensor molecules with varying characteristics. For example, when using perylene as the aromatic core, the five-membered imide rings may be positioned to form "Z-shaped" perylenes in which the imide rings form each end of the "Z."

The aromatic sensor molecules may also include sensor groups that are attached to the amine moiety of the five-membered imide rings. When sensor groups with sufficiently strong electron donating capability are attached to the nitrogen atoms on the imide rings, they can quench the excited state of the aromatic core by photoinitiated intramolecular electron transfer and reduce its fluorescence intensity and quantum yield as well as shift its fluorescence spectrum to longer wavelengths. The sensor groups can be selected from specific groups that interact with target analytes in a variety of ways, such as covalent bond formation, electron transfer or complexation. By such interaction, a specific chemical compounds or families of compounds (i.e., target analytes) can be detected. Interaction (e.g., chemical reaction) between the analyte and imide nitrogen substituents (i.e., the sensor group) disrupts intramolecular electron transfer from these substituents to the aromatic core resulting in either increases or decreases in the fluorescence intensity of the aromatic imide sensor molecule.

Figure 2:
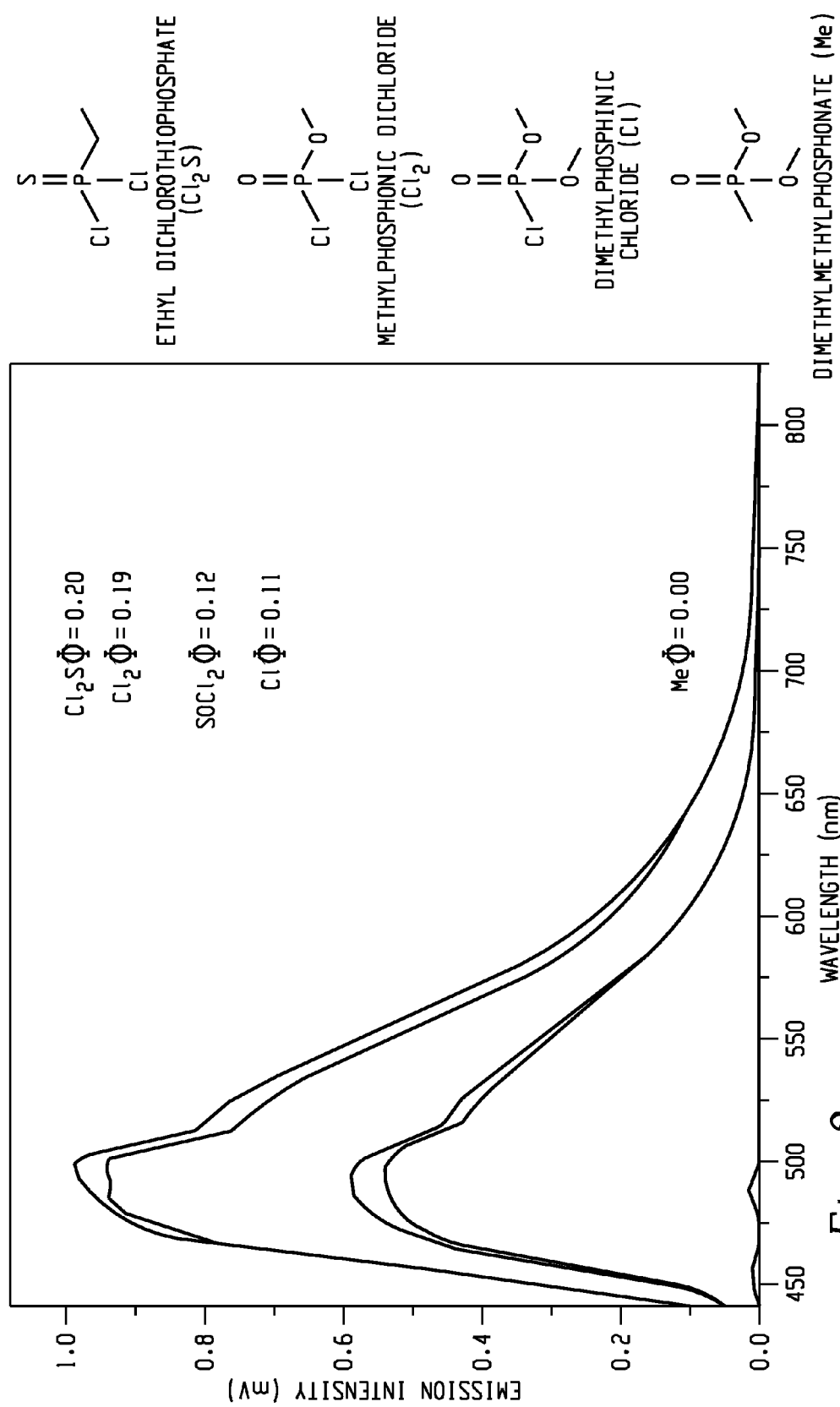
FIG. 2 shows the relative normalized emission spectra for N,N'-bis(p-aminophenyl)-1,5-bis(p-tetraethyleneglycoloxy) phenyl)anthracene-2,3,6,7,-tetracarboxyl bisimide in the presence of excess dCTP, MPdC, dMPC, thionycl chloride, and dMMP, respectively, from highest to lowest curve. Spectra were recorded in anhydrous DMF with 425 nm excitation.

Sensor groups on the imide ring nitrogen atoms are conjugated with the aromatic core and have the potential to increase or quench (decrease) the intensity and quantum efficiency of the fluorescence from the core. Sensor groups can be selected to interact with certain chemical or biochemical analytes via a chemical reaction, electron transfer process, or complexation. Such interactions, in turn alter the fluorescence behavior of the imide. For example, addition of a 4-aminophenyl group to the imide nitrogen of a 1,5-diaryl-2,3,6,7-anthracene tetracarboxyl diimide (Meador, et al., *Chem. Mater.* 2004, 16, 2978) produces a diimide that does not fluoresce. While the anthracene core is highly fluorescent, the amine nitrogen of the 4-aminophenyl substituent transfers a free electron to the anthracene core. This excited state electron transfer process is so efficient that it completely quenches the fluorescence of the anthryl diimides. However, chemical reactions such as protonation with the 4-aminophenyl nitrogen atom, ties up its free electrons and the excited state electron transfer is no longer possible. As a result, the diimides is now fluorescent. FIG. 1 shows the effect of adding thionyl chloride on fluorescence quantum yield of this molecule. With no added thionyl chloride, this diimide has a quantum yield of 0. However, addition of trace amounts (parts per million or less) of thionyl chloride activates the sensor molecule fluorescence and the quantum yield increases with increasing thionyl chloride concentration to an upper limit of 0.15. Similarly, addition of reactive phosphoryl esters, compounds that are structurally similar to Sarin nerve gas, also activates the fluorescence of this sensor molecule. The effects of adding several of these compounds to the sensor molecule are shown in FIG. 2. Reactive phosphoryl esters, such as phosphoryl chlorides activate the sensor molecule. However, addition of dimethyl methylphosphonate, an unreactive phosphoryl ester, does not. This demonstrates that the sensor molecule is only activated by compounds similar to Sarin and does not react with those that are not, thereby avoiding the occurrence of "false-positives".

Various sensor molecules can be used to provide different types of aromatic sensor molecules. For example, replacement of a 4-aminophenyl sensor group with a benzo crown ether, such as benzo 15 crown-5, produces a compound which is only weakly fluorescent. In this case, the two oxygen substituents are not as efficient an electron donor as the nitrogen atom in the previous example and, hence, excited state electron transfer from these oxygens only partially quenches the fluorescence of the anthracene core. Addition of sodium ions, which complexes with the oxygen within the crown ether and further reduces their electron donating capability, leads to an increase in fluorescence of this anthryl diimides. Replacement of the 4-aminophenyl substituent with an N,N,N-triphenylamine produces an anthryl diimde which fluoresces. This fluorescence can be quenched by exposure of the diimide to nitroaromatic compounds, similar to 2,4,6-trinitrotoluene used in explosives. In this case, intermolecular electron transfer from the triaryl amine substituent to the nitroaromatic analyte quenches the excited state of the diimides and the fluorescence intensity is reduced. For a further description of this electrochemistry, see James et al., *J. Am. Chem. Soc.* 1995, 117, 8982-8987), which is incorporated herein by reference. Such a reversal of quenching causes the aromatic sensor molecule to fluoresce more brightly, thereby assuming the "on" state.

By selection of an appropriate structure for the sensor group, the aromatic sensor molecules may be configured to detect a wide variety of different target analytes. The target analyte, as defined herein, is a chemical or group of chemicals that the aromatic sensor molecule has been configured to detect. For example, the target analyte may be hydrogen ions for aromatic sensor molecules configured to detect changes in pH. Other examples of target analytes include metal ions, chemical warfare compounds (e.g. organophosphates), explosives (e.g. nitroaromatic compounds), and carbohydrates. Anthracene diimide compounds including aniline sensor groups prepared by the inventors have demonstrated the ability to detect various organophosphate compounds. See Meador et al., *Chem. Mater.*, 2004, 16, 2978, the disclosure of which is incorporated by reference herein. Examples of suitable sensor groups include aryl-crown ethers, aryl amines, porphyrins, and phenyl boronic acid. In the case of aryl-crown ethers, it is further noted that the aryl-crown ethers can be configured to recognize different ions as a result of changes in the diameter of the alkyether ring used. Examples of aryl-crown ethers include various benzo-crown ethers such as benzo-15-crown 5 ether, benzo-18-crown-6 ether, and benzo-24-crown-8 ether, as well as naphthyl ethers (e.g. di-2, 3-naphtho-30-crown-10 ether) and dibenzo ethers (e.g., dibenzo-18-crown-6 ether).

The aromatic sensor molecules also include at least two pendant bulky groups on the core. For example, the aromatic sensor molecules may include two pendant bulky groups, or they may include four pendant bulky groups. The pendant bulky groups are preferably aryl groups, such as phenyl or napthyl groups, heteroaryl groups, or bulky alkyl groups (e.g., t-butyl groups). Most preferably, the pendant bulky groups are pendant aryl groups. If the bulky groups include substituents (e.g., a hydroxy group), preferably, but not necessarily, this substituent is present on all of the pendant bulky groups to facilitate their synthesis. The pendant bulky groups may improve the stability and fluorescence of aromatic sensor molecules. For example, the pendant aryl groups may improve the fluorescence of the aromatic sensor molecule by using steric crowding to prevent self-quenching in excited states. In addition, the pendant bulky groups provide improved oxidative and photo-stability. For example, aromatic diimide molecules of the present invention may be stable in aqueous solution, and/or may be stable in air when exposed to ultraviolet radiation for 48 hours or more.

The pendant bulky groups may also be used to alter properties of the aromatic sensor molecule such as its solubility in aqueous solution or its fluorescence. For example, the solubility of the aromatic sensor molecules may be affected by attaching tetraethyleneglycoloxy groups to the pendant aryl groups. Fluorescence of the aromatic sensor molecule, on the other hand, may be altered as a result of, for example, steric effects or electron donating or withdrawing effects. Alteration of the fluorescence may result in different absorption, emission, and/or intensity of the fluorescence. Additional substituents may be provided on the pendant aryls, such as those selected from the group consisting of hydrogen, alkyl, haloalkyl, halogen, alkoxy, cyano, nitro, amino, alkylamino, carboxyl, and hydroxyl moieties.

The pendant bulky groups may also serve to provide a point of attachment for the aromatic sensor molecules to other materials. To serve as a point of attachment, the pendant bulky groups (e.g., pendant aryl groups) may be provided with moieties that allow the aromatic sensor molecules to be attached to substrates, such as a polymer or nanoparticles. For example, thiol groups may be provided to allow the attachment of the aromatic diimide molecules to gold surfaces.

Alternate embodiments of the invention may include substituents attached to the amines of the five-membered imide rings that do not interact with a target analyte, such as sensor molecules designed to detect molecular strain rather than specific analytes, as discussed further herein.

Aromatic sensor molecules of the present invention may provide high fluorescence quantum yields. Higher fluorescent quantum yields are preferable, as they provide greater sensitivity and other advantages. As known by those skilled in the art, the fluorescence quantum yield ($\Phi_F$) is the ratio of photons absorbed to photons emitted through fluorescence, as opposed to being deactivated by another, non-radiative mechanism. For example, aromatic sensor molecules of the present invention may have a fluorescence quantum yield of about 0.1 or higher. In some embodiments, higher quantum yields such as yields greater than about 0.15 or about 0.2 are provided. The fluorescence quantum yield of a compound may be readily determined through the use of well characterized standard samples with known $\Phi_F$ values, as described by Williams et al., *Analyst*, 1983, 108, 1067, which is incorporated by reference herein. Aromatic sensor molecules of the present invention may provide sensitivities in the parts-per million range, or in some embodiments, in the parts-per billion range.

In addition to providing high fluorescence quantum yields, the aromatic sensor molecules of the present invention may be tuned through choice of aromatic core and/or the various substituents attached to the core to provide compounds with fluorescent emission at a variety of different wavelengths. For example, fluorescent aromatic molecules of the present invention exhibit peak fluorescence at wavelengths that vary from about 450 to about 800 nanometers (nm). By use of differing aromatic cores and substituents, aromatic sensor molecules can be provided that exhibit peak fluorescence at wavelengths from about 450 to about 550, from about 550 to about 650, and from about 650 to about 800. For example, use of an anthracene aromatic core generally provides fluorescent emission of about 500 nm, whereas large polycyclic aromatic hydrocarbons used in the aromatic core may provide emission spectra of about 700 nm or more. Increasing the steric crowding around the aromatic core of the aromatic diimide molecule may be used to decrease the wavelength of the fluorescence, whereas the addition of electron donors on the sensor group and/or the pendant aromatic groups may be used to increase the wavelength of the fluorescence.

In addition to providing novel fluorescent compounds, the present invention is directed to methods of detecting, and optionally quantifying the concentration of a target analyte in a sample, comprising: a) adding to a sample the aromatic sensor molecules; b) measuring the resulting fluorescence of the sample; and c) determining whether the target analyte is present in said sample, and optionally the concentration of the target analyte in the sample. In some cases the process of detection is reversible over a plurality of repeating cycles, during which the target analytes associate with the sensor group resulting in fluorescence, and then dissociate to reset the sensor for renewed use. However, reversible detection is not required, and is not provided in other embodiments such as those in which the sensor molecule bonds to its target analyte.

Fluorescence by the aromatic sensor molecules may be detected by essentially any suitable fluorescence detection device. Such devices are typically comprised of a light source for excitation of the fluorophore and a sensor for detecting emitted light. In addition, fluorescence detection devices typically contain a means for controlling the wavelength of the excitation light and a means for controlling the wavelength of light detected by the sensor. Such means for controlling wavelengths are referred to generically as filters and can include diffraction gratings, dichroic mirrors, or filters. Examples of suitable devices include fluorimeters, spectrofluorimeters and fluorescence microscopes. Many such devices are commercially available from companies such as Hitachi, Nikon or Molecular Dynamics.

In general, assays using the aromatic sensor molecule provided by the present invention involve contacting a sample with the aromatic sensor molecule (or vice versa) and measuring fluorescence. The presence of a target analyte that interacts with the aromatic sensor molecule increases the fluorescence of the aromatic sensor molecule as a result of counteracting or decreasing the quenching of the sensor molecule by the sensor groups. Essentially any change in fluorescence caused by the target analyte may be used to determine the presence of the target analyte and, optionally its concentration, in the sample. Typically, the fluorescence will change in intensity. For example, in on-off sensors, will only provide significant fluorescence when they have detected a target analyte, and otherwise will not fluoresce or will fluoresce at a dramatically lower level. In other embodiments, the change in fluorescence may be a change in the emission frequency.

The excitation or absorbance spectrum is the wavelengths of light capable of causing the aromatic sensor molecule to fluoresce. To determine the excitation spectrum, different wavelengths of light are tested sequentially for their abilities to excite the sample. For each excitation wavelength tested, emitted light is measured. Emitted light may be measured across an interval of wavelengths (for example, from 450 to 700 nm) or emitted light may be measured as a total of all light with wavelengths above a certain threshold (for example, wavelengths greater than 500 nm). A profile is produced of the emitted light produced in response to each tested excitation wavelength, and the point of maximum emitted light can be referred to as the maximum excitation wavelength. A change in this maximum excitation wavelength, or a change in the shape of the profile caused by target analyte in a sample may be used as the basis for determining the presence, and optionally, the concentration of the target analyte in the sample. Alternatively, the emission spectrum may be determined by examining the spectra of emitted light in response to excitation with a particular wavelength (or interval of wavelengths). A profile of emissions at different wavelengths is created and the wavelength at which emission is maximal is called the maximum emission wavelength. Changes in the maximum emission wavelength or the shape of the profile that are caused by the presence of a target analyte in a sample may be used to determine the presence or concentration of the target analyte in the sample.

Various substrates can be coated with the aromatic sensor molecules of the present invention to be used as probes to determine the presence or absence of target analytes. The fluorescent sensor compounds of the present invention may be used in both homogeneous and heterogeneous binding assay formats, and can be easily attached to solid surfaces. In heterogeneous binding assays, arrays of different fluorescent aromatic compounds may be provided on the same or proximate substrates for the detection of various target species or species families. For example, a single substrate can be functionalized with two or more aromatic sensor molecules, each of which will react with different target analytes to activate their respective fluorescent emission, thereby determining which of numerous target analytes are present based on the specific emission wavelength that occurs. The detection of heterogenous target analytes may be conducted simultaneously or sequentially in a heterogeous binding assay.

Fluorescent aromatic compounds may be bound to various surfaces, including sol-gel materials, mesoporous materials (e.g., aerogels), glass and gold surfaces, silica and polymer based nanoparticles, and various other polymers and resins. For a discussion of the use of fluorescent compounds in various materials, see Basabe-Desmonts et al., *Chem. Soc. Rev.*, 2007, 36, 993-1017, the disclosure of which is incorporated herein by reference. In addition, the sensor compounds are well suited for applications in numerous particle-based and flow cytometry assays known in the art. Note that in additional embodiments, the aromatic compounds are not attached to a surface, but rather are merely added to a medium in which the aromatic sensor compounds are soluble or otherwise supported.

In a particle-based assay, the aromatic sensor compounds of the invention may either be attached to the surface or incorporated into the body of a solid particle. The solid substrate may be a micro particle, ranging, for example from about 0.1 to about 20 micrometers. The particles are preferably round and uniform, such as commonly available polystyrene latex particles formed by emulsion polymerization. They may be produced of other materials and by other processes that are known in the art. Examples of the materials and methods include, but are not limited to, plasticized polyvinyl chloride (PVC) particles produced by droplet casting of dissolved polymers or glass-like particles produced from sol gels. Solid particles may be hydrophilic particles such as, but not limited to, controlled pore glass (CPG) beads or a polymer gel.

For biomedical applications the aromatic sensor compounds of the invention can be immobilized in a biocompatible polymer matrix to form an implantable sensor. Preferably, the biocompatible polymer matrix is permeable to the target analyte. For use in biomedical applications, nontoxic aromatic molecules are preferably used. The toxicity of a number of the aromatic molecules (e.g. anthracene based aromatic diimide sensor compounds bearing diamine, diphenyl, triphenyl, and dicyano sensor groups) of the present invention at 100 μM and 1 mM doses was evaluated in mammalian cells (e.g., LS174T colon carcinoma cells), with the diamine compounds exhibiting no adverse effects at either concentration. Suitable biocompatible polymer matrices used for medical implants are known in the art. The fluorescent sensor compounds may be covalently bound to the polymer matrix using techniques such as those described in U.S. Pat. No. 6,002,954, which is hereby incorporated by reference. Such methods generally involve adding a suitable tether to the molecule such that the tether can be used to covalently attach the compound to the matrix.

Whether attached to a surface or dispersed in a medium the aromatic sensor molecules can be used for various applications. For example, the sensor molecules may be used for homeland security and defense by detecting explosives and/or chemical warfare agents or for use in preparing tamper-indicating paint. The sensor molecules can also be used to detect pH changes and metal ions, which may be useful, for example, as sensors for water and air quality monitoring. The sensor molecules can also be used to detect various analytes such as glucose for biomedical applications. The sensor molecules can also be used in material science for tasks such as monitoring polymer cure and degradation. The fluorescent aromatic compounds of the present invention can also be used for a wide variety of other applications requiring fluorescent compounds, such field effect transistors (FETs), organic light emitting diodes (OLEDs), photodynamic therapy, and as fluorescent tags for proteins and DNA.

As described herein, the aromatic compounds of the present invention may be tuned through alteration of their structure to fluoresce at a variety of different wavelengths. In addition, the aromatic compounds of the present invention may fluoresce at different wavelengths in response to changes in their environment. For example, the aromatic compounds may fluoresce at one wavelength in the open air, and then another wavelength when placed in solution. In addition, the aromatic compounds may fluoresce at different wavelengths in different solutions. For example, aromatic compounds may exhibit a red shift (i.e., shift to emission longer wavelengths) when place in more polar solvents. The change of fluorescence observed upon change in environment may be used to allow embodiments of the aromatic sensor invention to function as sensors outside of their capacity to detect specific target analytes as a result of interaction with the sensor groups. An example of this would be the use of aromatic compounds to detect an increase in polarity in a solution by a red shift in their fluorescent emission.

Another example of the ability of aromatic compounds of the present invention to detect changes in their environment is the ability of aromatic compounds to change their fluorescence in response to the application of mechanical stress. While not intending to be bound by theory, aromatic compounds may exhibit changes in their emission wavelength as a result of the formation of excited state complexes known as exciplexes in which the aromatic compounds stack atop one another. For example, aromatic diimides including perylene as the aromatic core may shift from emission in the green region to the red region as the result of exciplex formation. The shift of emission wavelength resulting from the formation of complexes of aromatic compounds enables the use of fluorescent aromatic compounds as molecular strain gauges. Strain gauges may be used to detect whether a structure has been subject to significant mechanical stress, and help provide warning when materials are under stress or have been damaged. These types of aromatic compounds can be incorporated into various materials (e.g., polymers) where they then function as molecular strain gauges.

Compounds of the invention may be synthesized by synthetic routes that include processes analogous to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v 1-6, Pergamon Press, Oxford, England, (1995); or Barry M. Trost and Ian Fleming, *Comprehensive Organic Synthesis*, v. 1-8, Pergamon Press, Oxford, England, (1991)).

For illustrative purposes, the reaction schemes described herein provide potential routes for synthesizing the compounds of the present invention as well as key intermediates. Aromatic diimides including anthracene aromatic cores may be prepared by the Diels-Alder cycloaddition reactions of bis-o-quinodimethanes, which are generated in situ by the photoenolization of o-methylphenyl ketones. Photolysis of o-methylbenzophenone then produces a pair of hydroxyl-o-quinodimethane isomers via a 1,4-biradical intermediate, of which the 3E isomer can be trapped by Diels-Alder cycloaddition with dienophiles such as dimethyl acetylenedicarboxylate to product the corresponding cycloadducts, as shown in Example 1 below. Dehydration of this compound and subsequent aromatization yields highly substituted anthracene derivatives. The functionalized diketones may be prepared by reaction between the corresponding dinitriles and appropriate Grignard reagents followed by hydrolysis under acidic conditions. Z-shaped perylene, phenanthrene, and benzo[e]pyrene diimides may also be prepared using this process. See Meador et al., *Org. Lett.*, 2006, 8, 577 and Meador et al., *J. Am. Chem. Soc.* 2006, 128, 702, which describe the synthesis of these aromatic diimides and are incorporated by reference herein.

Figure 3B:
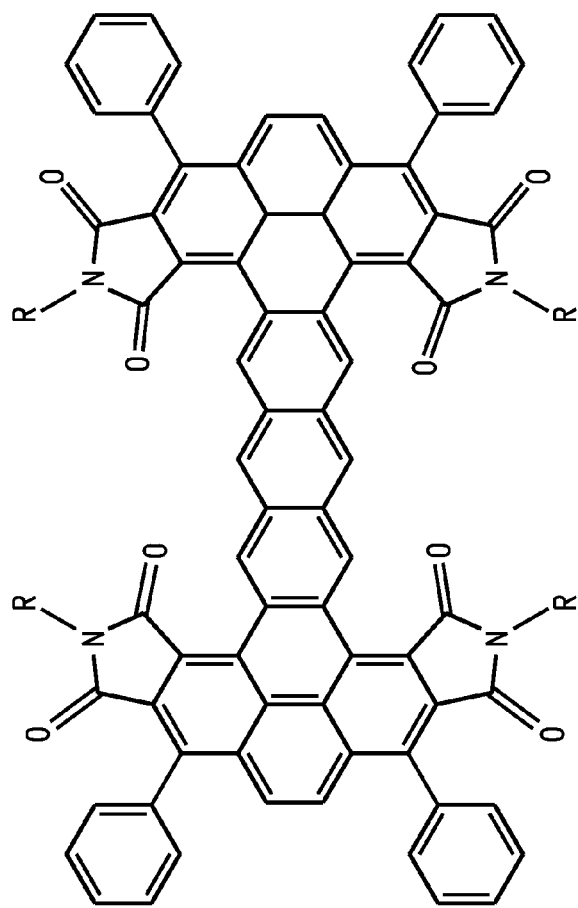
FIG. 3 shows two exemplary large polycyclic aromatic diimide sensor molecules (3a and 3b) that may be prepared using described methods.
Figure 3A:
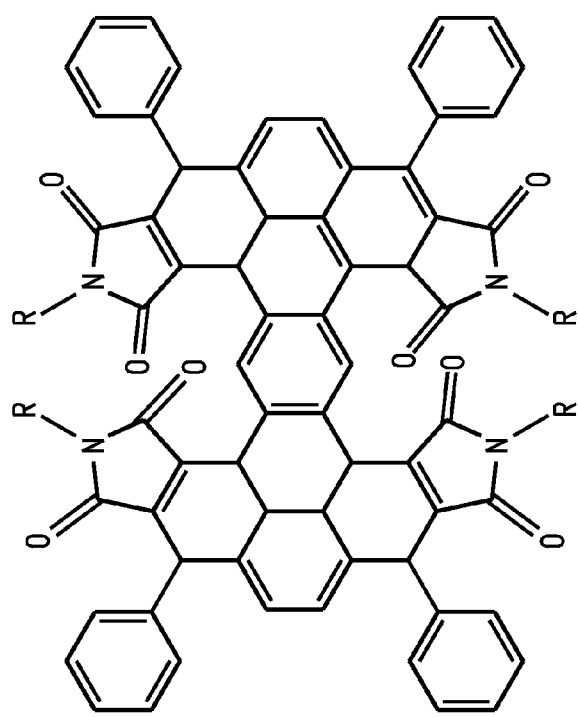

Alternately, anthracene diimides may be prepared by reacting 1,5-bis(phenyl)anthracene-2,3,6,7-tetracarboxyl dianhydride with a primary alkylamine by refluxing in a suitable organic solvent in the presence of an acid. The bisanhydride is prepared by the same Diels-Alder trapping process described above. However, dimethyl acetylenedicarboxylate is used as the dienophile. Hydrolysis of the methyl esters in the resulting bisadduct and cyclodehydration affords the corresponding dianhydride. For more detailed description of the individual reaction steps for either of these processes, see the EXAMPLES section below. Either of these reaction schemes may also be used to prepare large polycyclic aromatic hydrocarbons, such as those shown in FIG. 3.

Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

EXAMPLES

The invention will be further described by reference to the following detailed examples. These examples are offered to further illustrate the various specific and preferred embodiments and techniques. It should be understood, however, that many variations and modifications may be made while remaining within the scope of the present invention.

Example 1

Tunable Fluorescence of Anthracene Diimides

A number of anthracene diimides were synthesized utilizing Diels-Alder cycloaddition reactions of bis-o-quinodimethanes, which are generated in situ by the photoenolization of o-methylbenzophenone derivatives. As shown is Scheme 1, photolysis of o-methylbenzophenone (1) by 18 hour irradiation produces a pair of hydroxyl-o-quinodimethane isomers (3Z and 3E) via a 1,4-biradical intermediate (2). The quinodimethane isomer, 3Z, is unstable and reverts to the starting material with high efficiency. However, 3E, can be trapped by Diels-Alder cycloaddition with dienophiles, including dimethyl acetylenedicarboxylate (3d).

Scheme 1.
General photoenolization procedure using o-methylbenzophenone (1) and Diels-Alder trapping using dimethyl acetylenedicarboxylate.

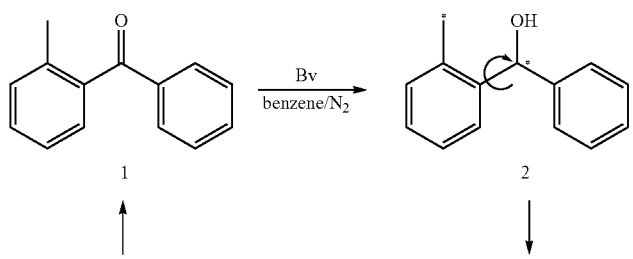

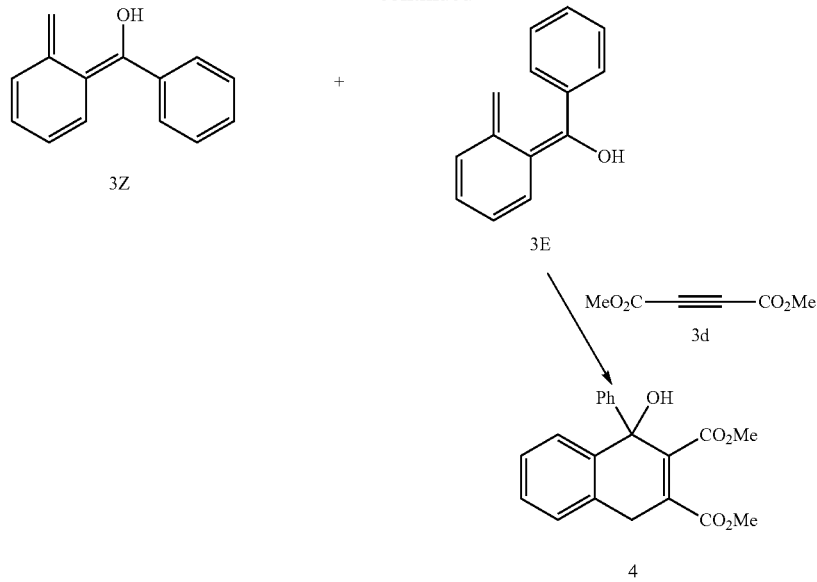

Figure 4:
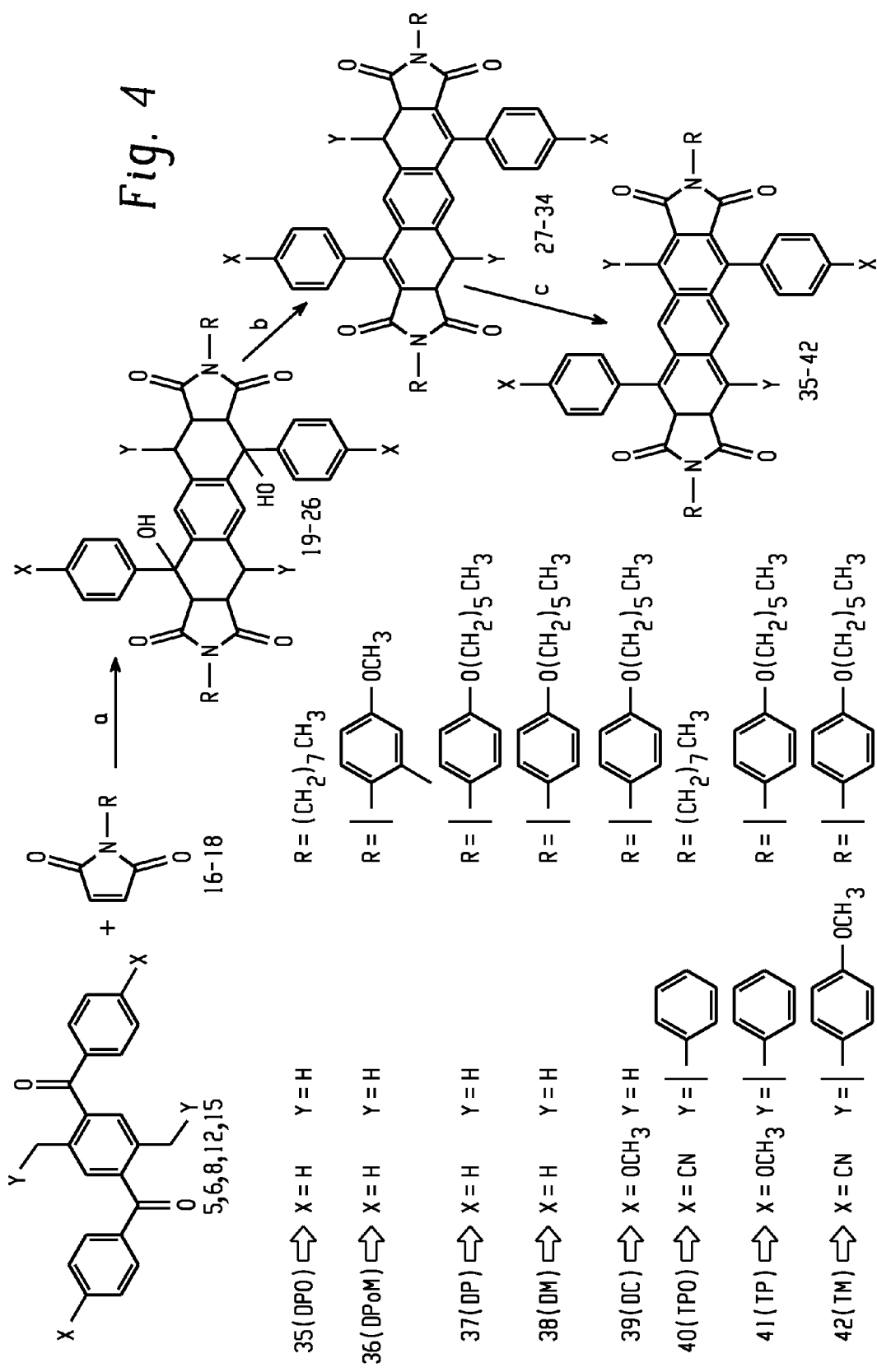
FIG. 4 shows a synthetic methodology for the preparation of highly substituted anthracence diimides.

Step 1: Hydrogen abstraction
Step 2: Biradical yields photoenols E and Z
Step 3: E participates in Diels-Alder reactions To prepare anthracene diimides, 2,5-dibenzoyl-p-xylene derivatives are photoenolized, followed by trapping to product a bisadduct which is then dehydrated and aromatized to yield substituted anthracene derivatives. The compounds that were provided using this process are shown in FIG. 4. The reagents used for the steps shown are (a) hv, benzene; (b) p-toluene sulfonic acid monohydrate, toluene; and (c) DDQ, chlorobenzene or sulfur in diphenylether.

Unless otherwise stated, all experiments used optically dilute solutions (Optical Density (OD)<0.2) at room temperature. Fresh samples were prepared for all measurements by dissolving the appropriate analyte in the appropriate solvent followed by serial dilutions until an acceptable OD was obtained. Luminescence solutions were prepared under atmospheric conditions and held in anaerobic 1 cm² quartz cells (Starna or Spectracell) during interrogation. Absorption spectra were measured with a Shimadzu scanning spectrophotometer (UV-3101 PC). Emission spectra were obtained with an Aminco-Bowman luminescence spectrometer (Series 2). The excitation was accomplished with a 150 W Xe lamp optically coupled to a monochrometer (+2 nm). The emission was collected at 900 and passed through a second monochrometer (±2 nm). Luminescence was measured with a photomultiplier tube (PMT). Radiative quantum yields ($\Phi_r$) were measured against either anthracene ($\Phi_r$=0.27 in EtOH) or [Ru(bpy)$_3$](PF6)$_2$ ($\Phi_r$=0.062 in CH$_3$CN) and calculated using the following equation $$\Phi_{unk} = \Phi_{std} \left(\frac{I_{unk}}{A_{unk}}\right)\left(\frac{A_{std}}{I_{std}}\right)\left(\frac{\eta_{unk}}{\eta_{std}}\right)^2$$

where unk represents the sample, std represents the standard, $\Phi$ is the radiative quantum yield, I is the integrated emission intensity, A is the absorbance at the excitation wavelength, and $\eta$ is the refractive index of the solvent.

Luminescence lifetimes were measured with an IBH time-correlated single photon counting (TCSPC) system equipped with an IBH Model TBX-04 Photon Detection Module. The excitation source for the TCSPC measurements was a pulsed LED (IBH NanoLED, 455 nm, 1.3 ns pulse duration or 403 nm, <200 ps pulse duration) with a repetition rate of 1 MHz. All data was analyzed by iterative reconvolution of the decay profile (10,000 counts at the peak channel) with the instrument response function using software provided by the instrument manufacturer.

Figure 5:
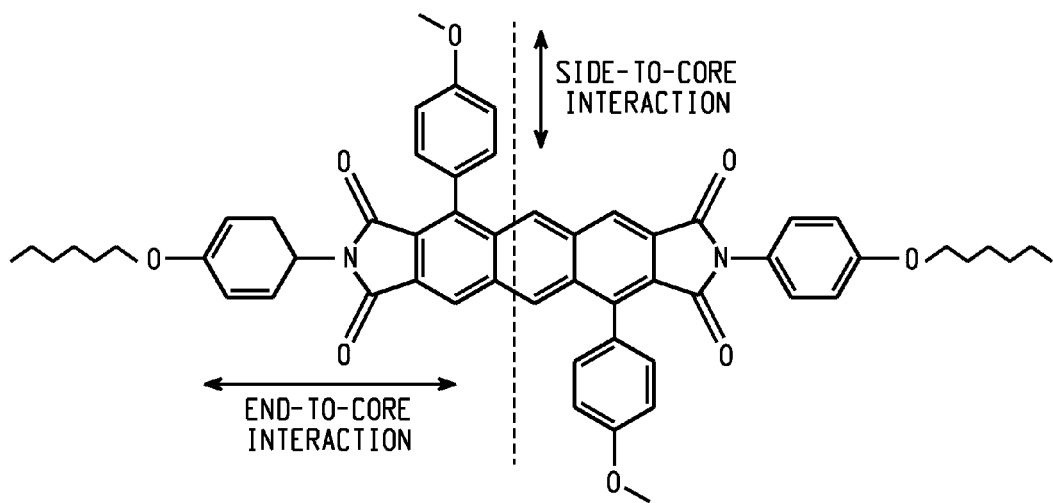
FIG. 5 shows the different functional regions of a representative anthracence diimide.

Based on the structure of the anthracene diimide molecules, several electronic interactions are possible, including electron transfer and inductive effects. Directional interactions are also likely due to the rigid spatial arrangement of the pendant, substituted phenyls. FIG. 5 shows several of the basic functional regions of an aromatic diimide. Specifically, the figure shows the aromatic core in the middle, the five-membered imide rings on each end, and anthracene linked pendant aromatic groups on the top and bottom. The major electronic interactions (both electron transfer and inductive) are indicated by double ended arrows. FIG. 5 further reveals the two main areas of directional interaction; end-to-core (imide-to-anthracene) and side-to-core (pendant phenyl units-to-anthracene). It was observed (vide infra) that anthracene diimides display both electron transfer and inductive interactions. Furthermore, electron transfer is favored in the end-to-core channel while inductive effects are enhanced for the side-to-core orientation.

All of the anthracene diimide derivatives presented in this example follow a generic naming system to quickly identify the substitution pattern. For example, DPO (35) represents diphenyl octyl; the first name indicates the side functionality (in this case, two phenyl groups) and second name indicates the imide functionality (in this case, an aliphatic octyl group). Derivatives with hexyloxy phenyl units on the ends do not include a reference to the end groups in the abbreviated name because most of the derivatives are substituted with hexyloxy phenyl groups. Refer to FIG. 4 for a complete account of names and functionality.

Following the described nomenclature, the simplest or electronically least complicated anthracene diimide derivative is DPO (35), which consists of two phenyl rings attached as pendants to the anthracene core (on the sides) and two octyl units linked through the imides (on the ends). Replacement of the octyl unit with a hexyloxy phenyl group produced DP (37). Addition of methoxy or cyano groups to the unsubstituted phenyls gave DM (38) and DC (39), respectively. Together, the four compounds constitute the substituted diphenyl anthracene diimide series. Tabulated spectroscopic and photophysical data for the diphenyl series are presented in Table 1.

(37) in toluene showed multiple, overlapping bands. Increasing the solvent polarity has the effect of decreasing the intensity of the high energy component while decreasing the energy of the second component. The lifetime drops from 620 ps in toluene to below 200 ps in ethyl acetate and solvents of higher polarity. The quantum yield concomitantly fell from 0.18 in toluene to 0.0082 in acetone. These observations indicate the presence of multiple excited states in DP (37); the first state being a localized π-π* transition and the second being a charge-transfer excited state. In addition, because the

TABLE 1

Spectroscopic and photophysical data of DPO (35), DM (38), DP (37), and DC (39) in solvents of increasing polarity.

| Solvent (Dielectric) | Abs. $\lambda_{max}$ (nm)$^a$ | | | | Em. $\lambda_{max}^b$ (nm) | | | | $^1\tau(ns)^c$ | | | | $\Phi_r$ | | | |
|---|---|---|---|---|---|---|---|---|---|---|---|---|---|---|---|---|
| | DPO | DM | DP | DC$^d$ | DPO | DM | DP | DC | DPO | DM | DP | DC | DPO | DM | DP | DC |
| Toluene (2.4) | 422 | 428 | 422 | 417 | 437(p) | 462(p) 488(s) | 497(p) 525(p) | 505(s) 543(p) | 6.36 | 1.25 | 0.62 | 0.39 | 0.35 | 0.18 | 0.066 | 0.046 |
| CHCl$_3$ (4.8) | 426 | 431 | 428 | 425 | 437(p) | 465(p) 491(s) | 501(p) 536(p) | 504(s) 555(p) | 5.79 | 0.59 | 0.38 | 0.27 | 0.36 | 0.064 | 0.028 | 0.025 |
| Ethyl Acetate (6.02) | 420 | 425 | 421 | 418 | 433(p) | 463(p) 488(p) 526(p) | 500(s) 555(p) | 573(p) | 6.90 | 0.30 3.60 | <0.20 | <0.20 | 0.34 | 0.028 | 0.015 | 0.012 |
| THF (7.6) | 421 | 426 | 422 | 420 | 435(p) | 463(p) 494(p) 538(p) | 502(s) 562(p) | 579(p) | 6.71 | 0.27 2.88 | <0.20 | <0.20 | 0.37 | 0.021 | 0.017 | 0.013 |
| C$_2$H$_4$Cl$_2$ (10.7) | 424 | 430 | 426 | 425 | 436(p) | 463(p) 490(s) 526(p) | 502(s) 557(p) | 571(p) | 5.60 | 0.34 | <0.20 | 0.21 | 0.46 | 0.030 | 0.020 | 0.017 |
| Acetone (20.1) | 421 | 426 | 423 | 423 | 435(p) | 463(p) 492(p) 554(p) | 500(s) 584(p) | 599(p) | 7.29 | <0.20 3.76 | <0.20 | <0.20 | 0.37 | 0.011 | 0.0082 | 0.0062 |
| ACN (38.8) | 423 | 427 | NS$^e$ | 423 | 435(p) | 463(p) 487(s) 551(p) | NS$^e$ | 600(p) | 8.03 | <0.20 3.27 | NS$^e$ | <0.20 | 0.46 | 0.0087 | NS$^e$ | 0.0051 |

$^a$Represents the approximate center of the longest wavelength absorption band.
$^b$Represents the approximate center of the most intense emission bands. A shoulder is indicated by the symbol (s) and a peak by the symbol (p).
$^c$TCSPC using 370 nm pulsed LED excitation and iterative reconvolution.
$^d$Represents the lowest energy absorption shoulder due to an absence of a clear peak.
$^e$Indicates low solubility that prevented data collection.

The quantitative absorption spectra of the diphenyl series were prepared. The inductive effects to the HOMO/LUMO gap could be seen as a shift in the absorption maximum for DP (37), DM (38), and DC (39). DP (37) can be used as the baseline, or reference, as this derivative has a low potential for inductive interaction with the pendant groups (the effects of the end groups will be discussed later). The absorption maximum of DM (38) was red shifted in relation to DP (37) while the absorption maximum of DC (39) was blue shifted. The methoxy substituents have the potential to inductively donate electron density to the anthracene diimide core, resulting in a lower energy HOMO/LUMO gap and a lower energy absorption band. The cyano groups have the opposite effect as they are more likely to inductively pull electron density from the core and increase the energy gap. The absorption spectrum of DPO (35) was expected to be similar to DP (37) because there was no substitution on the side phenyls. The absorption spectrum of DPO (35), however, was at slightly higher energy than DP (37). This is likely due to small differences in the electronic perturbation of the anthracene diimide core between the octyl groups of DPO (35) and the hexyloxy phenyl groups of DP (37).

The normalized emission spectra of DPO (35) and DP (37) in a variety of solvents were obtained. In all solvents, DPO (35) showed a single, vibrationally structured emission band with a lifetime between 5 and 8 ns and a radiative quantum yield between 0.34 and 0.46. The emission spectrum of DP structural differences between DPO (35) and DP (37) are on the ends, it is reasonable to suggest that the charge-transfer component is an end-to-core interaction.

Figure 6:
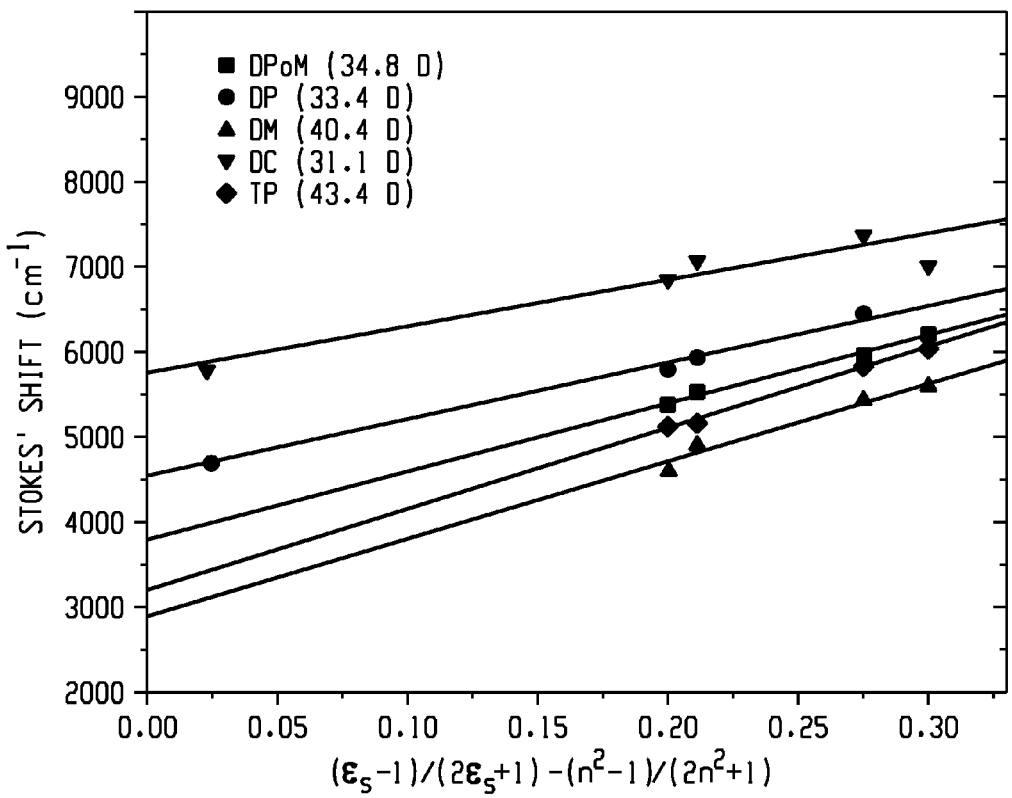
FIG. 6 shows the relationship of the Stokes shift and Lippert-Mataga polarity parameter for DPoM, DP, DM, DC, and TP. The calculated dipole change for each chromophore is listed in the figure legend.

The solvatochromic response of the anthracene diimides to photoexcitation was further characterized by analysis of the Stokes' shift and Lippert-Mataga polarity parameter, $$\bar{v} = \frac{1}{4\pi hc\varepsilon_0} \frac{(\Delta\mu)^2}{\alpha^3} \left( \frac{\varepsilon_s - 1}{2\varepsilon_s + 1} - \frac{n^2 - 1}{2n^2 + 1} \right) + C$$

where $\bar{v}$ is the Stokes' shift in wavenumbers, h is Plank's constant, c is the speed of light, $\varepsilon_0$ is the permittivity of free space, $\Delta\mu$ is the change in the dipole moment upon excitation, $\alpha^3$ is the molecule's volume, as is the solvent dielectric constant, and n is the solvent refractive index. This relationship quantifies the change in dipole between the ground state and excited state of a molecule and, when used with the calculated ground state dipole, the magnitude of the excited state dipole moment may be estimated. The Lippert-Mataga correlations of the anthracene diimide series are shown in FIG. 6. Each line represents a solvatochromic emission component of the corresponding diimide. All other bands were not solvatochromic and not included in the analysis. For example, the emission spectra of DPO (35) in the selection of solvents were nearly identical and could not be used in the Lippert-Mataga correlations. DP (37) had two components in the emission profiles; a higher energy band that quickly disappeared with increasing solvent polarity and a lower energy component that red-shifted with increasing solvent polarity. According to the Lippert Plot, the second component displays a slope of 6,600.2 cm$^{-1}$ (R$^2$=0.99). Using the volume of 850.123 Å$^3$ from molecular modeling, the calculated dipole change (Δμ) is 1.114×10$^{-28}$ C m or 33.4 D. This data further supports the existence of a polar excited state for DP (37).

The normalized emission spectra of DM (38) and DC (39) in a variety of solvents were obtained. In general, the trends that were observed for DP (37) were also seen with DM (38) and DC (39). Specifically, the quantum yields of both DM (38) and DC (39) decreased with increasing solvent polarity and the lifetime of DC (39) quickly decreased to the instrument limited response. The lifetime data for DM (38) is interesting as multiple exponential signals were measured in most polar solvents. These experiments confirm the presence of complex excited states and supports our assertion of a π-π* transition and a charge transfer component.

Further inspection of the emission spectra of DM (38) and DC (39) revealed the inductive effects associated with the side-to-core interaction. The electron withdrawing ability of the pendant cyano phenyl groups on DC (39) has the effect of allowing the charge transfer to occur efficiently even in the least polar solvent (toluene). In addition, the charge transfer excited state of DC (39) displays a 95 nm Stokes' shift from toluene to acetonitrile (31.1 D form the Lippert-Mataga correlation). The electron donating ability of DM (38) has a complex effect on its exited state behavior. In toluene, DM (38) has a single exponential lifetime with a quantum yield of 0.18. In acetonitrile, DM (38) has a multiple exponential decay with a quantum yield of 0.0087. In the later, however, the relative intensity of the low energy transition to the high energy transition is on the same order of magnitude. Also, transition from predominantly one excited state to multiple components is not smooth. First, ratios of the first component to the second component decrease, then increase, then decrease again as the solvent polarity increases. Second, the emission maximum of the lowest energy component red shifts, then blue shifts, then red shifts again as the solvent polarity increases. These observations indicate the inductive effects of the periphery side groups have a major affect on the electronic properties.

Three additional derivatives, TPO (40), TP (41), and TM (42), were synthesized to produce a substituted tetraphenyl anthracene diimide series. Here, TPO (40) is the reference compound while TP (41) and TM (42) contain additional units that will contribute to the excited state modulation. Tabulated spectroscopic and photophysical data for the tetraphenyl series are presented in Table 2.

TABLE 2

Spectroscopic and photophysical data of TPO (40), TM (42), and TP (41) in solvents of increasing polarity.

| Solvent (Dielectric) | Abs. λ$_{max}$ (nm)$^a$ | | | Em. λ$_{max}$$^b$ (nm) | | | $^1$τ(ns)$^c$ | | | Φ$_r$ | | |
|---|---|---|---|---|---|---|---|---|---|---|---|---|
| | TPO | TM | TP | TPO | TM | TP | TPO | TM | TP | TPO | TM | TP |
| Toluene (2.4) | 428 | 441 | 431 | 447(p) 468(p) | 480(p) | 482(p) 520(s) | 2.77 | 1.27 | 1.03 | 0.19 | 0.32 | 0.21 |
| CHCl$_3$ (4.8) | 432 | 444 | 435 | 447(p) 471(p) | 482(p) | 450(p) 482(p) 564(p) | 3.54 | 1.37 | 0.53 1.95 | 0.26 | 0.31 | 0.08 |
| Ethyl Acetate (6.02) | 426 | 436 | 428 | 442(p) 465(p) | 478(p) | 448(s) 499(s) 549(p) | 3.12 | 1.16 | 0.29 10.40 | 0.21 | 0.24 | 0.023 |
| THF (7.6) | 427 | 438 | 429 | 445(p) 467(p) | 479(p) | 459(s) 499(s) 552(p) | 3.03 | 1.16 | 0.30 7.43 | 0.20 | 0.24 | 0.027 |
| C$_2$H$_4$Cl$_2$ (10.7) | 430 | 441 | 435 | 445(p) 470(p) | 479(p) | 450(p) 478(p) 497(p) 549(p) | 3.19 | 1.19 | 0.37 7.78 | 0.23 | 0.25 | 0.029 |
| Acetone (20.1) | 427 | 437 | 429 | 443(p) 466(p) | 481(p) | 454(p) 576(p) | 3.34 | 0.83 | 0.2 11.40 | 0.21 | 0.14 | 0.011 |
| ACN (38.8) | 428 | 438 | 431 | 443(p) 468(p) | 481(p) | 456(p) 474(s) 585(p) | 3.84 | 0.54 | U$^d$ | 0.24 | 0.081 | 0.0080 |

$^a$Represents the approximate center of the longest wavelength absorption band.
$^b$Represents the approximate center of the most intense emission bands. A shoulder is indicated by the symbol (s) and a peak by the symbol (p).
$^c$TCSPC using 370 nm pulsed LED excitation and iterative reconvolution.
$^d$Indicates unreliable data likely due to a combination of low solubility, low quantum yield, and presumably complex decay kinetics.

The quantitative absorption spectra of the tetraphenyl series were obtained. It was reasonable to expect, since the additional units in the tetraphenyl series are pendant to the anthracene core, that the charge transfer behavior will be similar to the diphenyl series while the inductive effects will vary. In fact, the absorption spectrum of TPO (40) was similar to TP (41). The absorption maximum for TPO (40) was at slightly higher energy than TP (41) due to subtle differences in the end groups' electronic effects on the diimide core. The absorption maximum of TM (42) was red shifted with respect to the remainder of the tetraphenyl series. As postulated above, the lower energy absorption band is likely due to increased electron density on the anthracene diimide core resulting from the pendant methoxy substituents. The average difference between absorption maximums for TP (41) and TM (42), under the experimental parameters, was 7.6 nm. For DP (37) and DM (38), the average shift was 4.0 nm. This calculation suggests that increasing the number of side groups has an additive effect on the electronic properties.

The normalized emission spectra of TPO (40), TP (41), and TM (42) in a variety of solvents were obtained. The luminescence of TPO (40) was characterized by single, vibrationally structured band with peak maximum near 428 nm, a single exponential lifetime between 2.77 and 3.84 ns, and a quantum yield between 0.19 and 0.26. These data indicate the presence of a traditional $\pi$-$\pi^*$ transition. Incorporation of hexyloxy phenyls on the ends, TP (41), substantially changes the excited state properties. The emission spectrum of TP (41) shifted from a single band near 431 nm in toluene to a complex, solvatochromic spectrum in more polar solvents. The quantum yield also dramatically decreased during this transition and the radiative decay become complex. These experiments further support the existence of a $\pi$-$\pi^*$ transition in the octyl derivatives and both a $\pi$-$\pi^*$ transition and a charge transfer component in the hexyloxy phenyl derivatives.

The third chromophore in the tetraphenyl series, TM (42), showed a single emission band near 480 nm in all solvents. This is an interesting result considering the data up to this point has indicated that hexyloxy phenyl end groups produce multiple excited states, including a solvent dependant charge transfer transition. As discussed earlier, DM (38) showed complex behavior due to the electron donating effect of the side groups. This prevented a smooth, complete transition from a $\pi$-$\pi^*$ excited state to a charge transfer excited state. In comparison, the additional methoxy units on TM (42) have greater potential to increase the electron density of the anthracene diimide core by induction, resulting in no observable charge transfer emission band. This is likely due to further reduction of the HOMO/LUMO gap on the anthracene diimide core, which hinders the charge transfer event.

Figure 7A:
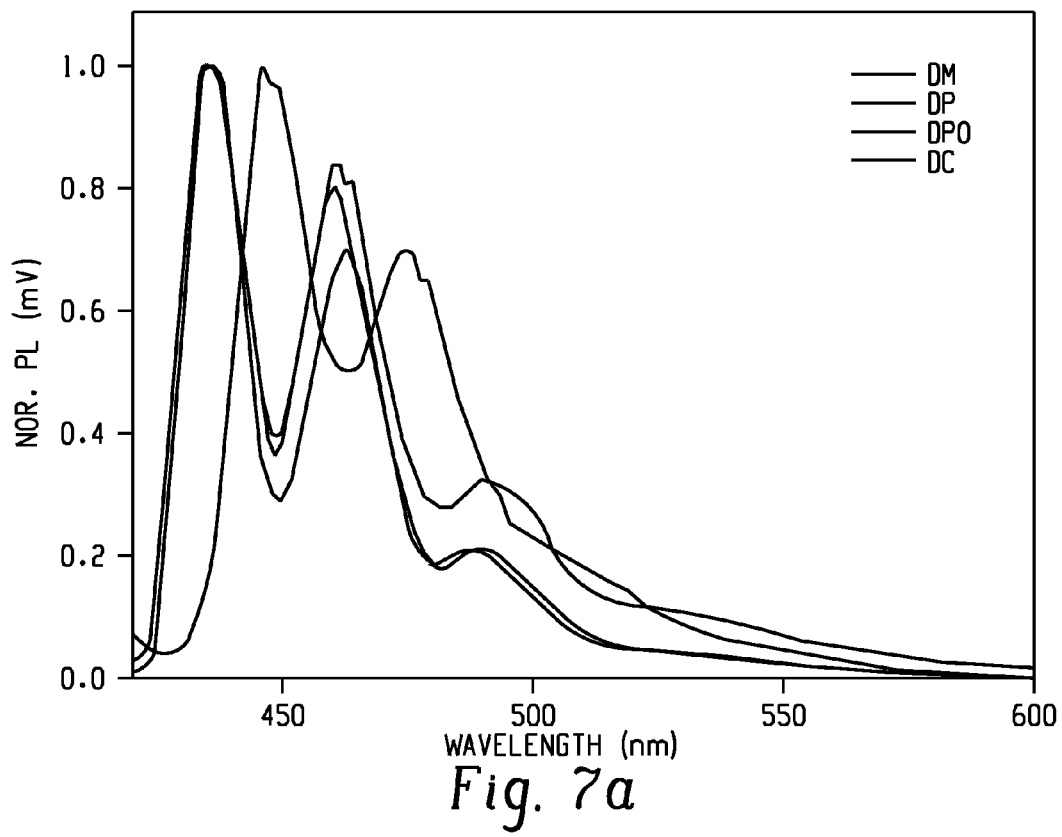
FIGS. 7a and 7b show normalized emission spectra for the diphenyl anthracene diimides (top) and the tetraphenyl anthracene diimides (bottom) at 77° K in 2-methyltetrahydrofuran and 405 nm excitation.
Figure 7B:
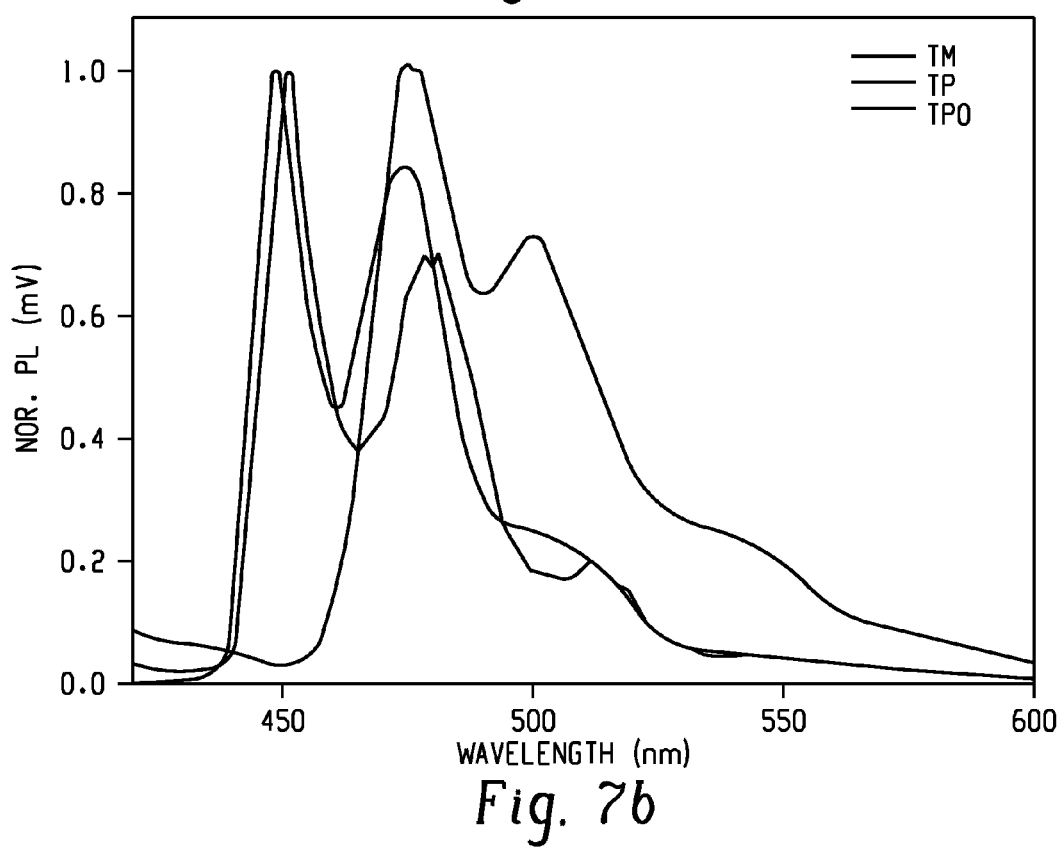

In an attempt to better understand the excited state properties of the diphenyl and tetraphenyl anthracene diimides, sub-ambient (77 K) emission experiments were performed, with the results shown in FIGS. 7a and 7b. In the case of the diphenyl derivatives, DPO (35), DP (37), and DC (39) display similar emission spectra with overlapping bands near 434 nm, 461 mm, and 492 nm. Although the peak ratios differ slightly, the band shapes and positions are nearly identical. Interestingly, DM (38) shows a lower energy emission spectrum (with a 13 nm red shift) while maintaining a similar band structure, which is consistent with the electron donating ability of the methoxy functionalized side groups. Similar results are observed for the tetraphenyl series. Here, TPO (40) and TP (41) display spectral features analogous to DPO (35), DP (37), and DC (39), but at lower energy. Furthermore, TM (42) shows the anticipated emission spectrum with an enhanced red shift of 26 nm, effectively doubling the inductive tuning of DM (38).

The energy levels of organic compounds are relatively insensitive to temperature changes. Low temperature experiments are often aimed toward measuring triplet properties, investigating excited state kinetics, or minimizing molecular entropy. Also, it has been demonstrated that structural and/or conformational changes, including loss of rotational freedom due to a rigid matrix (i.e. frozen glass), affects intramolecular electron transfer. An important observation of the diphenyl and tetraphenyl diimide low temperature experiments is the absence of charge transfer behavior. To investigate this phenomenon with respect to substituted anthracene diimides, DPoM (36) was synthesized and evaluated as a model with limited rotational freedom.

DPoM (36) is a diphenyl anthracene diimide with o-methyl p-methoxy phenyl end unit. The methoxy phenyl mimics the behavior of the hexyloxy phenyl while the metamethyl serves to obstruct the rotation by sterical interaction with the neighboring carbonyls. The absorption and emission spectra were obtained and the spectroscopic and photophysical data are summarized in Table 3. The absorption spectrum of DPoM (36) showed spectral features very similar to all other substituted diimides previously discussed, indicating minimal perturbation of the core electronic properties. The room temperature emission spectra exhibit comparable luminescence bands centered around 450 nm, previously assigned as a $\pi$-$\pi^*$ transition. As solvent polarity increases, an additional broad band appears near 575 nm, which has been attributed to a charge transfer interaction. In addition, the luminescence quantum yield decreases while the lifetime data become increasingly convoluted with increasing solvent polarity. These data further support the excited state assignments. Detailed inspection of the emission spectra, however, reveals the relative ratio between these two components ($\pi$-$\pi^*$ and charge transfer) is significantly lower than comparable, unhindered diimide derivatives. For example, DPO (35) started with a nearly one-to-one ratio of these two emission bands (based on peak height) in toluene and gradually ended with the disappearance of the first component ($\pi$-$\pi^*$) in acetone. In comparison, DPoM (36) did not reveal such dramatic changes. Here, the emission spectrum was dominated by the first component in all solvents. A small increase of the second component was measured with increasing solvent polarity indicating an inefficient charge transfer interaction. This may be explained by the rotational barrier of the metamethyl unit creating an unfavorable conformation.

TABLE 3

Spectroscopic and photophysical data of DPoM (36) in solvents of increasing polarity.

| Solvent (Dielectric) | Abs. $\lambda_{max}$ (nm)[a] | Em. $\lambda_{max}$[b] (nm) | $^1\tau(ns)$[c] | $\Phi_r$ |
|---|---|---|---|---|
| Toluene (2.4) | 423 | 442(p) | 4.76 | 0.27 |
|  |  | 463(p) |  |  |
|  |  | 494(s) |  |  |
| CHCl$_3$ (4.8) | 427 | 441(p) | 3.35 | 0.20 |
|  |  | 466(p) |  |  |
|  |  | 497(s) |  |  |
| Ethyl Acetate (6.02) | 421 | 437(p) | 4.12 | 0.036 |
|  |  | 460(p) | 0.84[d] |  |
|  |  | 494(s)[e] |  |  |
| THF (7.6) | 422 | 439(p) | 2.51 | 0.024 |
|  |  | 461(p) | 0.54[d] |  |
|  |  | 495(s)[e] |  |  |
| C$_2$H$_4$Cl$_2$ (10.7) | 426 | 440(p) | 1.56 | 0.084 |
|  |  | 465(p) |  |  |
|  |  | 498(s) |  |  |
| Acetone (20.1) | 422 | 438(p) | 3.29 | 0.010 |
|  |  | 462(p) | 0.24[d] |  |
|  |  | 496(s)[e] |  |  |
| ACN (38.8) | 425 | 439(p) | 3.85 | 0.011 |
|  |  | 463(p) | 0.24[d] |  |
|  |  | 494(s)[e] |  |  |

[a]Represents the approximate center of the longest wavelength absorption band.
[b]Represents the approximate center of the most intense emission bands. A shoulder is indicated by the symbol (s) and a peak by the symbol (p).
[c]TCSPC using 370 nm pulsed LED excitation and iterative reconvolution.
[d]Greater than 93% of the decay (i.e. the major component).
[e]A broad band or tail could be seen in these samples.

In conclusion, eight anthracene diimide derivatives were synthesized utilizing a versatile reaction sequence involving an important photochemical step. Two main series were developed, specifically diphenyl and tetraphenyl anthracene bisimdes, with varying degrees of electronic interaction. Photophysical investigations revealed two distinct emitting states, including a $\pi$-$\pi$* excited state and an intramolecular charge-transfer transition. Isolation of the emissive states through synthetic manipulation demonstrated a correlation between the charge transfer state and the cumulative inductive effects of the substituents. Finally, a control molecule was synthesized and evaluated, revealing the dependence of the charge transfer interactions on structural constraints.

Example 2

Synthesis of Chemosensory Anthracene Diimide Derivatives

Anthracene diimides, a previously difficult class of compounds to access, are characterized by visible absorption, green fluorescence, and photostability in the presence of oxygen. A systematic series was synthesized by a recently developed novel synthesis of substituted anthracene diimide derivatives using photoenolization of o-methylbenzophenones and Diels-Alder trapping. This procedure allowed for access to previously difficult to synthesize and insoluble anthracene diimide derivatives. While this procedure is useful, it requires four steps for each derivative. An anthracene bisanhydride starting material was developed so that many primary amines could be coupled with this compound in a one-step reflux reaction to create multiple anthracene diimide derivatives easily.

In this study, five new substituted anthracene diimide derivatives were synthesized and their chemosensory behavior was studied via absorption, emission, and lifetime spectroscopy, including excited-state kinetic, extinction coefficient, and quantum yield measurements. The R groups chosen for this new series of anthracene diimide derivatives were tert-butyl benzene, methyl 18-crown-6, benzo 15-crown-5, triphenyl amine, and phenyl boronic acid.

2,5-dimethyl-1,4-dicyanobenzene was custom synthesized by Aldrich. All other chemicals were purchased from Aldrich. All $^1$H NMR and $^{13}$C NMR spectra (300 MHz) were recorded using $CDCl_3$ as the solvent. Elemental analysis was obtained by Atlantic Microlabs, Inc. (Norcross, Ga.).

General Procedure for Coupling:

A mixture of 1,5-bis(phenyl)anthracene-2,3,6,7-tetracarboxyl bisanhydride in acetic acid was heated to 120° C., after which excess amine was added. The resulting mixture was refluxed at 120° C. for 18 hours. The mixture was filtered and washed with methanol. The precipitate was then boiled in methanol for 20 minutes, then filtered again and dried in a vacuum of at 65° C. This was followed by characterization to determine if the product was soluble in methanol or not.

(N,N'-Bis(p-(tert-butyl)phenyl)-1,5-bis(phenyl)anthracene-2,3,6,7-tetracarboxyl diimide (43): A mixture of 1,5-bis(phenyl)anthracene-2,3,6,7-tetracarboxyl bisanhydride (0.10 g, 0.22 mmol), 4-tertbutylanaline (140 μl, 1.54 mmol) in 5 ml of acetic acid was reacted and worked up according to the procedure for coupling yielding a yellow solid product (0.12 g, 77%). Calculated for $C_{50}H_{40}N_2O_4$: C, 81.94; H, 5.50; N, 3.82; O, 8.73. found C, 78.88; H, 5.51; N, 3.57. $^1$H NMR (300 MHz, $CDCl_3$): δ 1.32 (s, 18H), 7.35-7.49 (m, 8H), 7.52-7.64 (m, 10H), 8.58 (s, 2H), 8.69 (s, 2H). $^{13}$C NMR (300 MHz, $CDCl_3$): δ 31.30, 34.75, 124.06, 125.99, 126.08, 128.30, 128.53, 129.03, 130.02, 132.04, 133.67, 134.20, 134.54, 141.53, 151.43, 165.84, 166.16.

(N,N'-Bis(methyl 18-crown-6)-1,5-bis(phenyl)anthracene-2,3,6,7-tetracarboxyl diimide (44): A mixture of 1,5-bis(phenyl)anthracene-2,3,6,7-tetracarboxyl bisanhydride (0.10 g, 0.22 mmol), 2-(aminomethyl)-18-crown-6 (0.187 g, 0.64 mmol) in 5 ml of acetic acid was reacted and worked up according to the procedure for coupling. No desired product was in the solid. By characterizing the filtrate, it was determined that the product is soluble in methanol. The solvent from the filtrates was removed under vacuum. The product, yellow oil, was purified by dissolving it in dichloromethane and slowly dropping it into 100 ml of petroleum ether. The resulting mixture was filtered through a fine frit. The solid product was then stirred in 5 ml of ether for 20 minutes and filtered, yielding a yellow solid (0.134 mg, 6%). Calculated for $C_{56}H_{64}N_2O_{16}$: C, 65.87; H, 6.32; N, 2.74; O, 25.07. found C, 62.92; H, 6.04; N, 3.39. $^1$H NMR (300 MHz, $CDCl_3$): δ 3.50-4.10 (m, 50H), 7.26-7.75 (m, 10H), 8.422 (s, 2H), 8.581 (s, 2H).

(N,N'-Bis(benzo 15-crown-5)-1,5-bis(phenyl)anthracene-2,3,6,7-tetracarboxyl diimide (45): A mixture of 1,5-bis(phenyl)anthracene-2,3,6,7-tetracarboxyl bisanhydride (0.10 g, 0.22 mmol), 4'-aminobenzo 15-crown-5 (0.18 mg, 0.64 mmol) in 5 ml of acetic acid was reacted and worked up according to the procedure for coupling yielding a brownish-yellow solid. Product was dissolved and slightly heated in chloroform. The chloroform was removed via vacuum, and the final product, an orange-yellow solid, was dried in the oven (0.073 g, 34%). Calculated for $C_{58}H_{52}N_2O_{14}$: C, 69.59; H, 5.24; N, 2.80; O, 22.38. found C, 69.20; H, 5.39; N, 2.80. $^1$H NMR (300 MHz, $CDCl_3$): δ 3.75-4.17 (m, 32H), 6.91-7.01 (m, 6H), 7.52-7.56 (m, 10H), 8.55 (s, 2H), 8.66 (s, 2H). $^{13}$C NMR (300 MHz, $CDCl_3$): δ 113.073, 114,006, 119.773, 124,006, 125.039, 126.009, 128.2216, 129.975, 132.022, 133.701, 134.178, 134.564, 141.446, 149.226, 149.373, 165.789, 166.158.

4-aminotriphenylamine (48): A mixture of 4-nitrotriphenylamine (1.0 g, 3.44 mmol), 3 ml triethylamine, 5 wt. % palladium on carbon (0.475 g) in 15 ml DMF was cooled to 0° C. To this, a mixture of formic acid (1.3 g, 0.028 mol) in 10 ml of DMF was added dropwise over 15 minutes. After the addition, the reaction was heated at 70° C. for 2 hours. The palladium was filtered off and the reaction was rotavapped. The crude product was dissolved in 15 ml dichloromethane and filtered again to get rid of any remaining palladium. To this solution, 85 ml of dichloromethane and 10 ml of hexane was added. This was extracted with distilled water (4×25 ml), dried with sodium sulfate, filtered, and the solvent was removed via vacuum. The brown solid was recrystallized in ethanol. The resulting tan crystals were washed with ethanol and dried in a vacuum oven for an hour (171.6 mg, 19%). m.p. 148.1-148.5° C. $^1$H NMR (300 MHz, $CDCl_3$): δ 3.55 (s, 2H), 6.65 (d, 2H, J=9 Hz), 6.89-7.04 (m, 8H), 7.16-7.22 (m, 4H). $^{13}$C NMR (300 MHz, $CDCl_3$): δ 116.17, 121.48, 122.57, 127.82, 128.96, 139.00, 143.04, 148.33.

(N,N'-Bis(p-triphenyl amine)-1,5-bis(phenyl)anthracene-2,3,6,7-tetracarboxyl diimide (46): A mixture of 1,5-bis(phenyl)anthracene-2,3,6,7-tetracarboxyl bisanhydride (0.10 g, 0.22 mmol), triphenyl amine (0.16 g, 0.62 mmol) in 5 ml of acetic acid was reacted and worked up according to the procedure for coupling yielding an orangish-red solid. Product was dissolved and slightly heated in chloroform. The chloroform was removed by vacuum filtration and the final product, an orange-yellow solid, was dried in the oven (0.060 g, 30%). Calculated for $C_{66}H_{42}N_4O_4$: C, 83.00; H, 4.43; N, 5.87; O, 6.70. found C, 79.94; H, 4.49; N, 5.87. $^1$H NMR (300 MHz, CDCl$_3$): δ 7.01-7.33 (m, 28H), 7.52-7.65 (m, 10H), 8.57 (s, 2H), 8.68 (s, 2H) $^{13}$C NMR (300 MHz, CDCl$_3$): δ 123.23, 123.42, 124.04, 124.82, 125.43, 126.05, 127.36, 128.25, 128.56, 129.21, 129.38, 129.70, 132.04, 133.70, 134.22, 134.57, 141.49, 147.43, 147.83, 165.95, 166.19.

(N,N'-Bis(m-(boronic acid)phenyl)-1,5-bis(phenyl)anthracene-2,3,6,7-tetracarboxyl diimide (47): A mixture of 1,5-bis(phenyl)anthracene-2,3,6,7-tetracarboxyl bisanhydride (0.10 g, 0.22 mmol), 3-aminophenyl boronic acid monohydrate (0.99 g, 0.64 mmol) in 5 ml of acetic acid was reacted and worked up according to the procedure for coupling yielding a yellow solid. Product was dissolved in and heated slightly in chloroform. The chloroform was removed the photoenolization process and Diels-Alder trapping. In order to synthesize more substituted anthracene diimide derivatives more efficiently, 1,5-bis(phenyl)anthracene-2,3,6,7-tetracarboxyl bisanhydride was made in a large volume to simplify the subsequent amine coupling reactions. As depicted in Scheme 2, the functionalized diketone was prepared from 2,5-dimethyl-1,4-dicyanobenzene and the appropriate Grignard reagents followed by hydrolysis under acidic conditions. The diketone then underwent photoenolization and was trapped in a Diels-Alder cycloaddition with dimethyl acetylenedicoarboxylate acting as the dienophile. The photo adduct was dehydrated to fully aromatized the anthracene core, deprotected to replace the methoxy groups with hydroxyl groups, and ring-closed to create the final bisanhydride product.

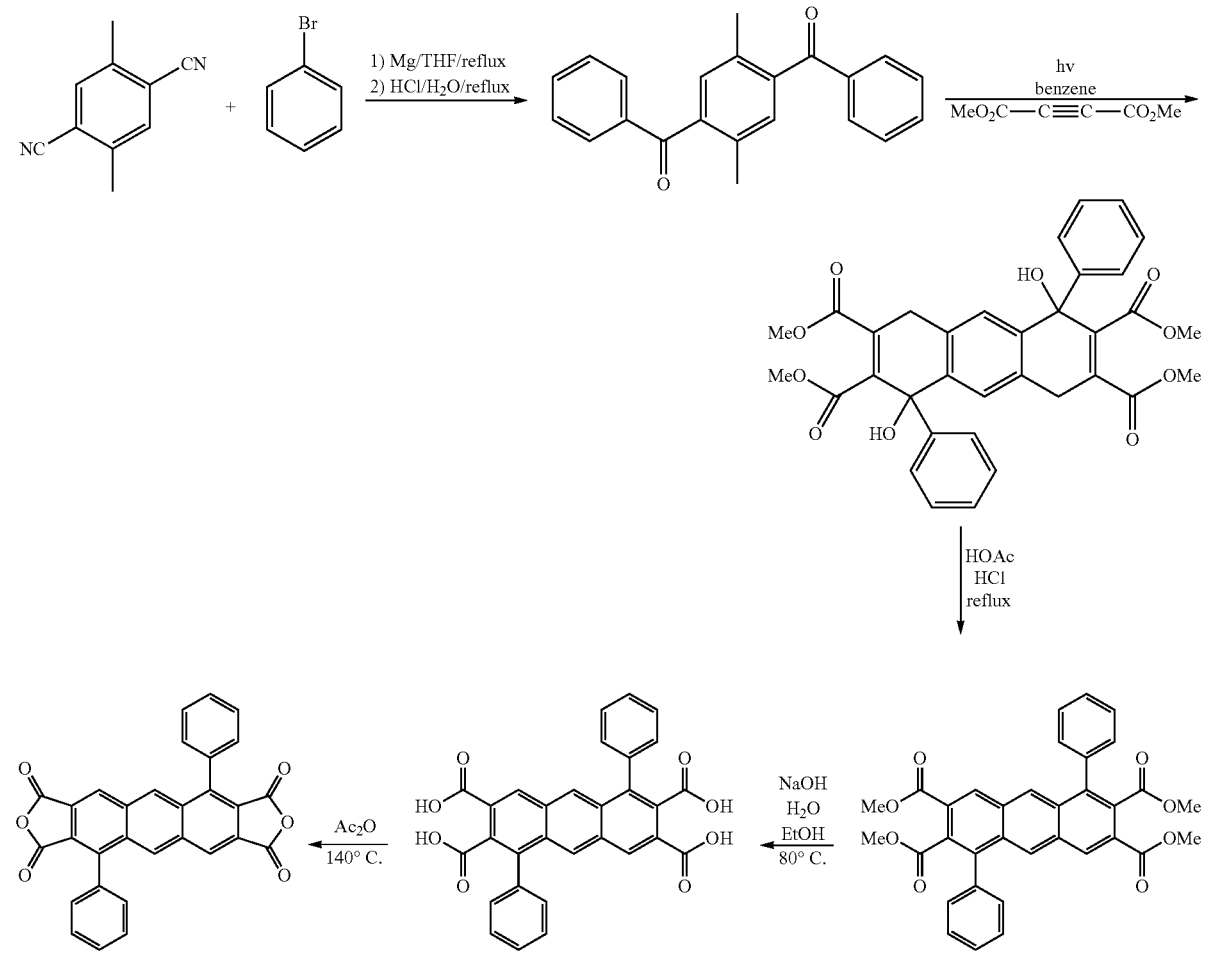

Scheme 2.
The synthesis of 1,5-bis(phenyl)anthracene-2,3,6,7-tetracarboxyl bisanhydride via Grignard reaction, photoenolization, and Diels-Alder trapping.

by vacuum filtration and the final product, a yellow solid, was dried in a vacuum oven. $^1$H NMR (300 MHz, CDCl$_3$): δ 7.31-7.63 (m, 9H), 8.52 (s, 1H), 8.63 (s, 1H).

As described in Example 1, anthracene diimide derivatives were previously synthesized via a 4 step procedure including The anthracene bisanhydride derivative is coupled with primary amines in a one-step reflux reaction at 120° C. in acetic acid (Scheme 3). Each anthracene diimide derivative was purified via several washings in methanol, and purified according to solubility.

Scheme 3.

The synthesis of substituted anthracene diimide derivatives using 1,5-bis(phenyl)anthracene-2,3,6,7-tetracarboxyl bisanhydride.

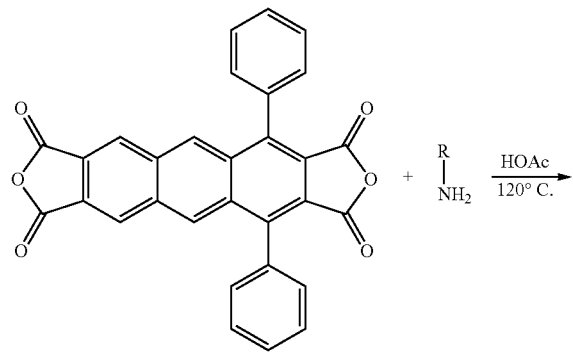

The R groups used in this study were tert-butyl benzene (43), benzo 15-crown-5 (44), methyl 18-crown-6 (45), triphenyl amine (46), and phenyl boronic acid (47), as shown below.

(43)

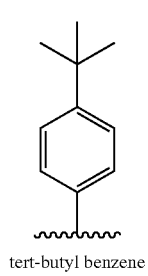

tert-butyl benzene (44)

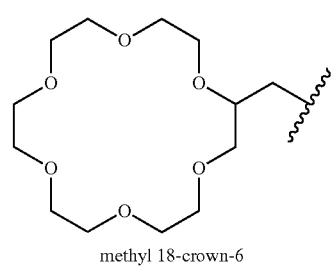

methyl 18-crown-6

(45)

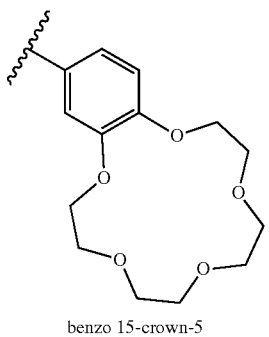

benzo 15-crown-5

(46)

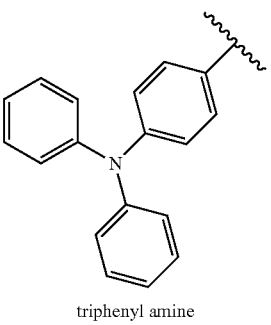

triphenyl amine (47)

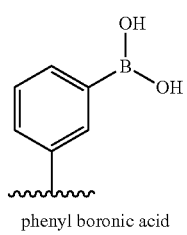

phenyl boronic acid

Anthracene diimide derivatives with each of these R groups were synthesized and characterized to determine the chemosensory potential.

Example 3

Chemosensory Activity of Anthracene Diimides

Unless otherwise stated, all experiments used optically dilute solutions (OD<0.2) at room temperature. Fresh samples were prepared for all measurements by dissolving the appropriate analyte in the appropriate solvent followed by serial dilutions until acceptable OD was obtained. Luminescence solutions were prepared under atmospheric conditions and held in anaerobic 1 cm² quartz cells (Stama or Spectracell) during interrogation. Absorption spectra were measured with a Shimadzu scanning spectrophotometer (UV-3101 PC). Emission spectra were obtained with a Horiba Jobin Yvon NanoLog. The excitation was accomplished with a 150 Watt Xe lamp optically coupled to a monochrometer (±2 nm). The emission was collected at 90° and passed through a second monochrometer (±2 nm). Luminescence was measured with a photomultiplier tube (PMT). Radiative quantum yields ($\Phi_r$) were measured against either anthracene ($\Phi_r$=0.27 in EtOH) and calculated using the following equation $$\Phi_{unk} = \Phi_{std}\left(\frac{I_{unk}}{A_{unk}}\right)\left(\frac{A_{std}}{I_{std}}\right)\left(\frac{\eta_{unk}}{\eta_{std}}\right)^2$$

Where unk represents the sample, std represents the standard, Φ is the radiative quantum yield, I is the integrated emission intensity, A is the absorbance at the excitation wavelength, and η is the refractive index of the solvent.

Luminescence lifetimes were measured with an IBH time-correlated single photon counting (TCSPC) system equipped with an IBH Model TBX-04 Photon Detection Module. The excitation source for the TCSPC measurements was a pulsed LED (IBH NanoLED, 455 nm, 1.3 ns pulse duration or 403 nm, <200 ps pulse duration) with a repetition rate of 1 MHz. All data was analyzed by iterative reconvolution of the decay profile (10,000 counts at the peak channel) with the instrument response function using software provided by the instrument manufacturer.

The tert-butyl benzene anthracene diimide derivative was synthesized as a model for the rest of the derivatives. No sensory behavior was detected for this model, as expected. The extinction coefficient, ∈, was determined to be 8,500 $M^{-1}$ $cm^{-1}$ and the quantum yield, Φ, 0.29 (both were measured in toluene). The lifetime was single exponential, again verifying the simple excited state, around 5.5 ns.

The methyl 18-crown-6 anthracene diimide derivative was synthesized because crown ethers are known for their ability to bind with metals. No sensory behavior was detected for this compound, possibly due to the missing phenyl group off of the imide. The extinction coefficient, ∈, was determined to be 12,500 $M^{-1}$ $cm^{-1}$ and the quantum yield, Φ, 0.37 (both were measured in toluene). The lifetime was single exponential, again verifying the simple excited state, ranging from about 5.5-6.5 ns depending on the solvent.

The phenyl boronic acid anthracene diimide derivative was synthesized because boronic acids are well-known for their ability to sense glucose. The lifetime was single exponential, again verifying the simple excited state, ranging from about 5-5.5 ns depending on the solvent.

Figure 8:
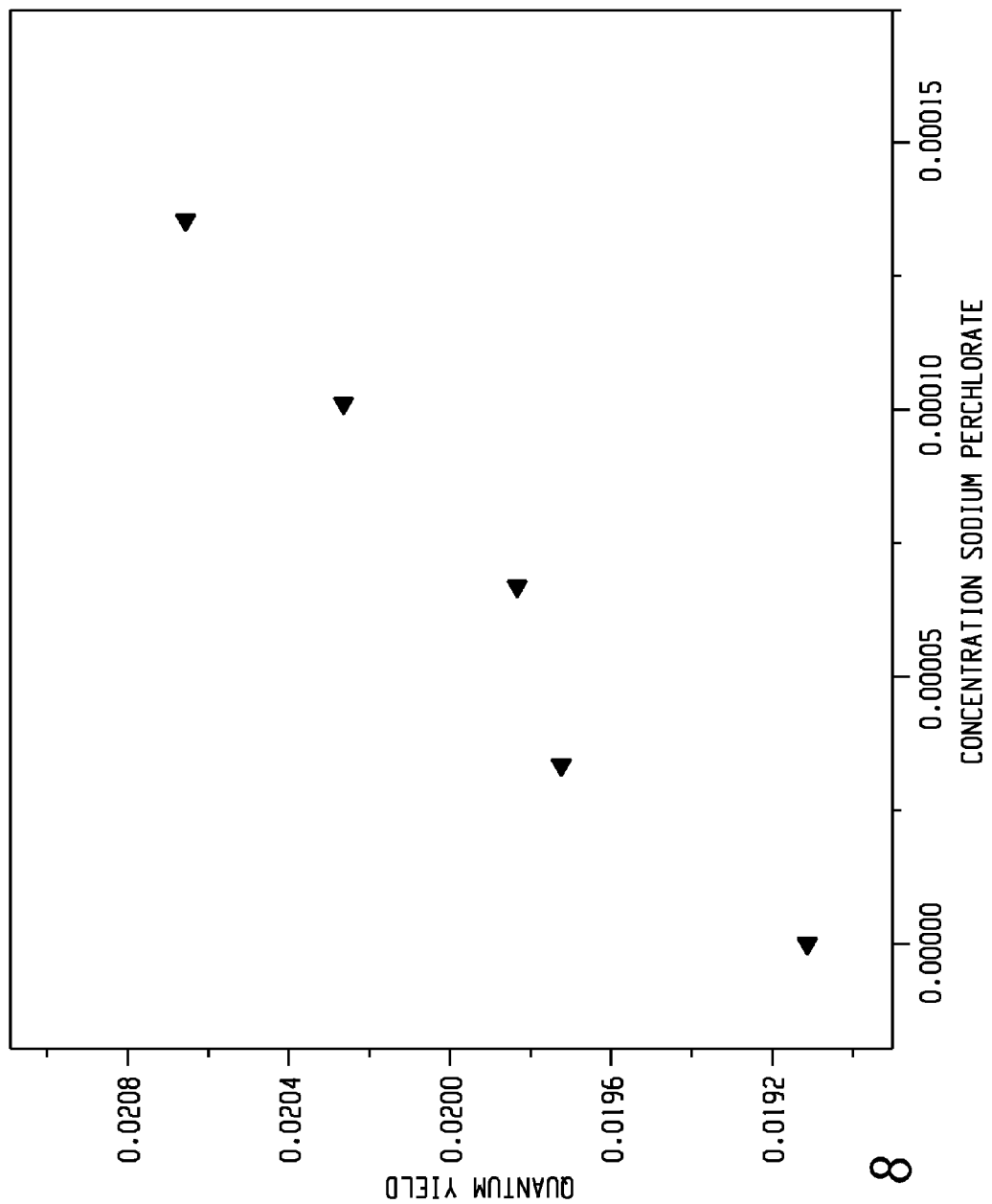
FIG. 8 shows the linear relationship between quantum yield and concentration of sodium perchlorate for an anthracene diimide benzo 15-crown-5 aromatic sensor.

The benzo 15-crown-5 anthracene diimide derivative was synthesized because crown ethers are known for their ability to bind with metals. This compound was shown to be a viable sodium sensor. The extinction coefficient, ∈, was determined to be 16,000 $M^{-1}$ $cm^{-1}$ and the quantum yield, Φ, 0.02 (both were measured in acetonitrile). The emission spectrum for this compound was more complicated than the others. An excimer effect was evident in higher concentration samples and was more prominent in non-polar solvents. The excimer complicated the lifetime in toluene with a short component for the excited dimer state. In acetonitrile, the benzo 15-crown-5 anthracene diimide derivative showed to be an effective sensor of sodium perchlorate, having a linear relationship between the concentration on sodium and the quantum yield of the compound, as shown in FIG. 8.

Figure 9A:
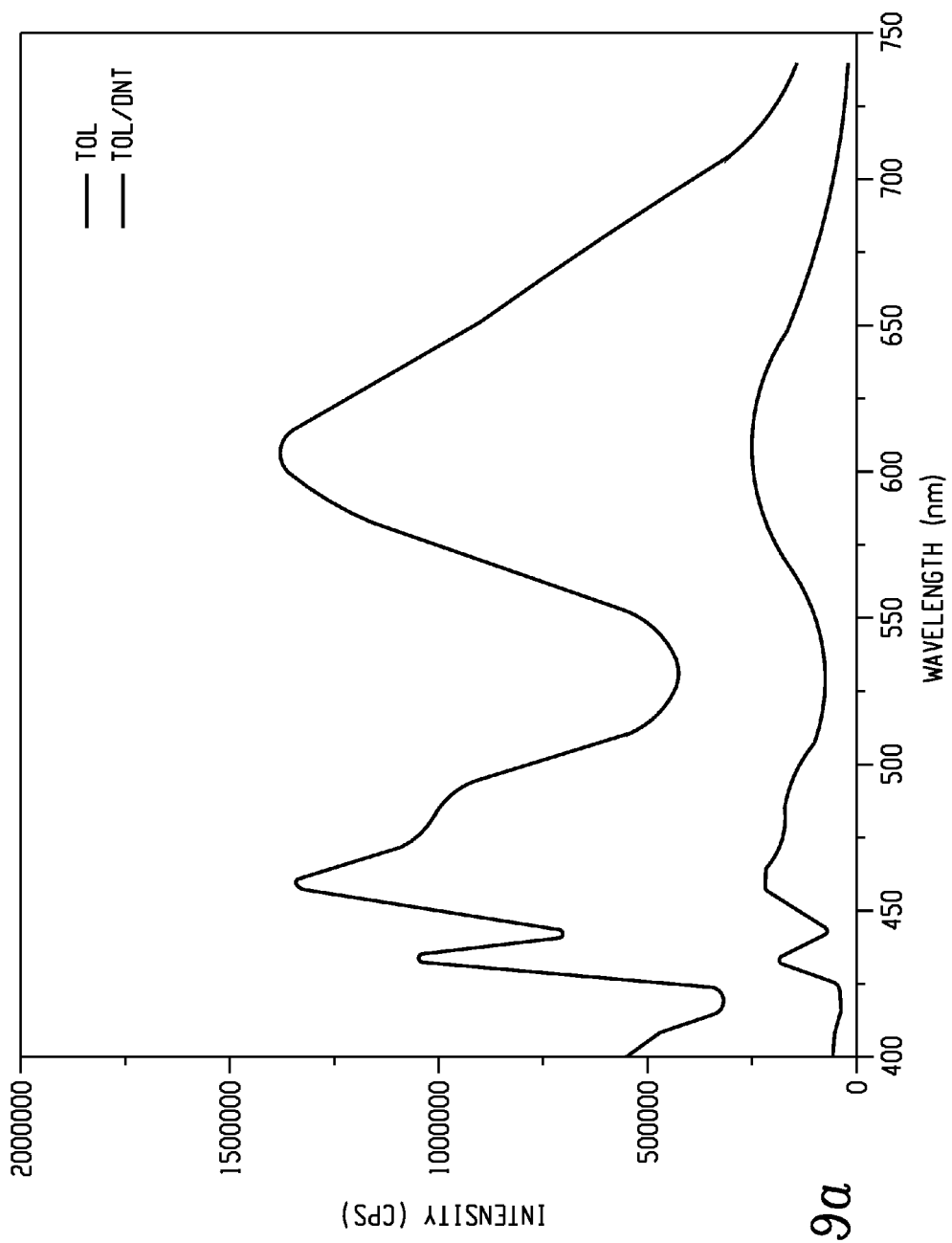
FIGS. 9a and 9b show emission spectra of concentrated and dilute samples of a triphenyl amine anthracene diimide derivative in toluene with dinitrotoluene as the quencher.
Figure 9B:
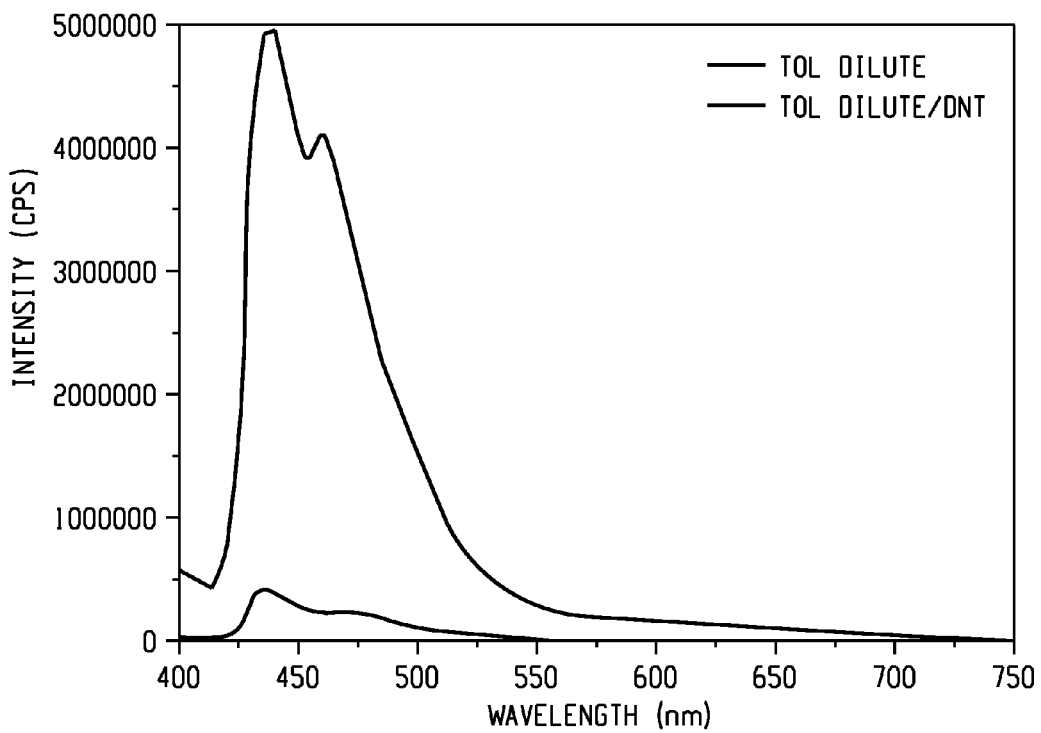

The triphenyl amine anthracene diimide derivative was synthesized because of its similar structure to other previously made sensing anthracene bisimde derivatives. This compound was shown to be an effective 2,4-dinitrotoluene (DNT) sensor, and therefore a possible trinitrotoluene or TNT sensor. The extinction coefficient, ∈, was determined to be 22,000 $M^{-1}$ $cm^{-1}$ and the quantum yield, Φ, 0.09 (both were measured in toluene). The emission spectrum for this compound was also showed an excimer in toluene. The excimer complicated the lifetime in toluene with a short component for the excited dimer state. In concentrated and dilute solutions of toluene (excimer and no excimer), 2,4-dinitrotoluene was shown to be an effective quencher of the triphenyl amine anthracene diimide derivative, as shown in FIGS. 9a and 9b. The Stem-Volmer relationship was used to quantify the rate coefficient of the quencher, $$\frac{I_f^0}{I_f} = 1 + k_q \tau_f [Q]$$

where $I_f^0$ is the intensity of the compound without any quencher, $I_f$ is the intensity of the compound with the quencher, $k_q$ is the rate coefficient of the quencher, $\tau_f$ is the lifetime of the compound without any quencher, and [Q] is the concentration of the quencher. Using this relationship $k_q$ was determined to be $1.02 \times 10^{11}$ $M^{-1}$ $s^{-1}$.

In conclusion, five anthracene diimide derivatives were synthesized using the new coupling procedure with anthracene bisanhydride starting material, and their chemosensory behavior was characterized. The benzo 15-crown-5 anthracene diimide was shown to be an effective sensor toward sodium and the triphenyl amine anthracene diimide derivative was proven to be a dinitrotoluene sensor, and therefore a potential TNT sensor.

Example 4

Synthesis of Perylene Diimides

Figure 10:
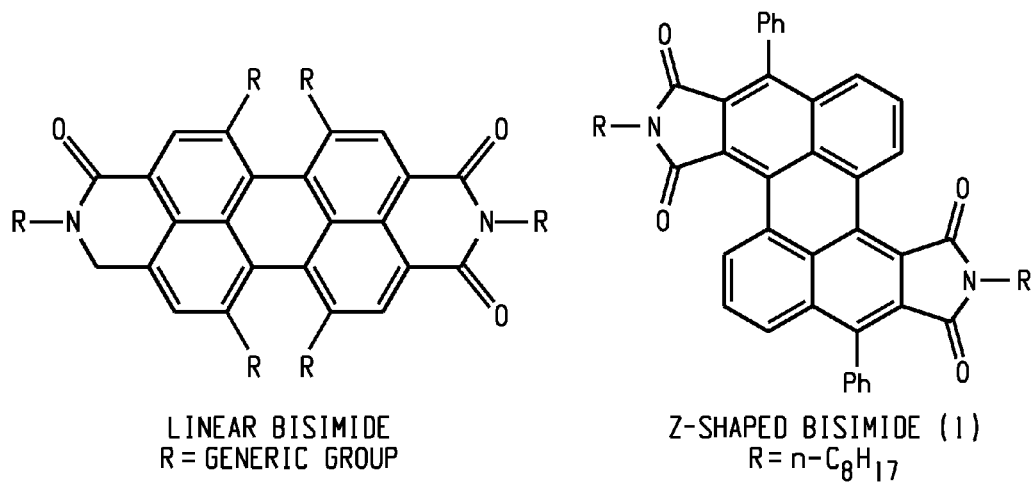
FIG. 10 shows a linear perylene and a Z-shaped perylene diimide (59).

The preparation of a non-linear or Z-shaped perylene diimide, 59 is described. This new diimide differs from conventional linear systems in both the position and size of the imide rings, as shown in FIG. 10. In addition, steric interactions between the imide carbonyls and hydrogens on C-6 and C-12 result in a twisting of the perylene ring system, as shown below. These changes, however, produce only minor electronic perturbations of the perylene diimide 59 and the favorable properties observed in linear systems, including visible absorption/emission and high fluorescence quantum yields, were retained.

Materials. All reagents were purchased from Aldrich and used as received. All $^1$H NMR and $^{13}$C NMR spectra (200 MHz or 400 MHz) were recorded using $CDCl_3$ or $d_6$-DMSO as solvent. Flash column chromatography was performed on silica with an Argonaut Flash Master II system equipped with a UV-Vis absorption detector. Elemental analysis was obtained by Atlantic Microlabs, Inc. (Norcross, Ga.).

1,5-dichloro-9,10-dihydro anthracene (50)

A mixture of 1,5-dichloro anthraquinone (49, 10 g, 36 mmol), red phosphorous (4.5 g, 145 mmol) and hydroiodic acid (47+%, 70 ml) in 470 ml of glacial acetic acid was refluxed under $N_2$ for 4 days. The resulting mixture was cooled to room temperature and poured into 1 L of water to precipitate a violet colored solid. The solid was collected by filtration, dissolved in 800 ml of $CH_2Cl_2$, and filtered again. The filtrate was washed once with 100 ml of $H_2O$, dried over $Na_2SO_4$ and concentrated under vacuum to yield the yellow colored, crude solid product. Methanol (100 ml) was added to this solid product and filtered again to collect white needles of the desired product (7.2 g, 80%). $^1$H NMR (300 MHz, $CDCl_3$): δ 4.10 (s, 4H), 7.12-7.25 (m, 6H). $^{13}$C NMR (300 MHz, $CDCl_3$): δ 32.93, 126.50, 127.13, 127.20, 133.15, 137.16.

1,5-dicyano-9,10-dihydro anthracene (51)

A mixture of 1,5-dichloro-9,10-dihydro anthracene (50, 6 g, 24.1 mmol), tris(dibenzylidene-acetone)dipalladium(0) (8 mol %, 1.776 g), 1,1'-bis(diphenylphosphino)ferrocene (16 mol %, 2.148 g), zinc (48 mol %, 0.768 g), and zinc cyanide (6.84 g, 58.3 mmols) in 120 ml of dry dimethyl acetamide (120 ml) was stirred under $N_2$ at 150° C. for 2 days. The resulting mixture was cooled to room temperature and poured into 700 ml of water to precipitate a brown colored solid. The solid was collected by filtration, dissolved in 900 ml of $CH_2Cl_2$ and filtered again to collect the filtrate. The filtrate was then washed once with 100 ml of $H_2O$, dried over $Na_2SO_4$, and concentrated under vacuum to yield a brown colored, crude solid product. Methanol (300 ml) was added to this solid product and filtered again to collect a dark cream colored product. The solid was dissolved in 300 ml of $CH_2Cl_2$ and filtered through silica. To the filtrate was treated with charcoal, filtered, and finally evaporated to dryness to yield pale yellow colored needles of the desired product (3.4 g, 61%). $^1$H NMR (300 MHz, $CDCl_3$): δ 4.23 (s, 4H), 7.34-7.62 (m, 6H). $^{13}$C NMR (300 MHz, $CDCl_3$): δ 33.88, 111.58, 117.60, 127.23, 131.01, 132.36, 135.92, 138.52.

9,10-dihydro anthracene-1,5-dicarboxylic acid (52)

A mixture of 1,5-dicyano-9,10-dihydro anthracene (51, 9 g, 36.9 mmol) and KOH (32.2 g, 0.57 mol) in 100 ml ethanol. The solution was refluxed under nitrogen with stirring for 18 hours. Water (20 ml) and HCl (20 ml) were added successively resulting in an orange-yellow precipitate. The mixture was added to 500 ml of water, filtered, and the solid was collected and dried under vacuum. The resulting green solid product was collected with a quantitative yield (According to NMR studies the product is 90+% pure). $^1$H NMR (300 MHz, $d_6$-DMSO): δ 4.34 (s, 4H), 7.25-7.30 (m, 2H), 7.51 (d, 2H, J=6 Hz), 7.70 (d, 2H, J=6 Hz), 13.00 (broad s, 2H). $^{13}$C NMR (300 MHz, $CDCl_3$): δ 33.26, 125.78, 127.84, 129.50, 131.01, 137.39, 138.08, 168.80.

1,5-dibenzoyl-9,10-dihydro anthracene (55)

A solution of 9,10-dihydro anthracene-1,5-dicarboxylic acid (52, 1 g, 3.73 mmol) in 200 µl of dimethyl formamide and 20 ml of thionyl chloride was refluxed for 3 hours. The resulting solution was evaporated to dryness under vacuum, 60 ml of benzene added, and warmed to 60° C. to obtain a solution. This solution was slowly added to a 250 ml round bottom flask containing a mixture of $AlCl_3$ and 20 ml of benzene. The resulting mixture was stirred for 18 hours at room temperature and poured into 100 ml of an ice/water mixture containing 10 ml of conc. HCl. The organic layer was separated and the aqueous layer was washed twice with 100 ml portions of benzene. After drying over $Na_2SO_4$, the combined organic extracts were dried under vacuum to yield a brown colored crude product. This was further purified by flash column chromatography to obtain a dark yellow, oily product (0.39 g, 27%) (According to NMR studies the product is 80+% pure). $^1$H NMR (300 MHz, $CDCl_3$): δ 4.04 (s, 4H), 7.20-7.86 (m, 16H), 7.51 (d, 2H, J=6 Hz), 7.70 (d, 2H, J=6 Hz), 13.00 (broad s, 2H). $^{13}$C NMR (300 MHz, $CDCl_3$): δ 33.95, 125.48, 126.98, 128.51, 128.55, 129.94, 130.30, 133.24, 135.74, 137.88, 197.15.

N-octyl maleimide (56): To a suspension of maleic anhydride (54, 5.4 g, 55 mmol) in 150 ml of benzene, a solution of octyl amine (53, 6.46 g, 50 mmol) in 100 ml of benzene was added. The resulting mixture was stirred at 30° C. for an hour and $ZnBr_2$ (12.4 g, 55 mmol) and hexamethyl disilazane (12.1 g, 75 mmol) in 30 ml of benzene were added. The resulting suspension was refluxed for 2 hrs. After cooling to room temperature, the reaction mixture was poured into 200 ml of 0.5 M HCl. The organic layer was separated and the aqueous portion was extracted twice with 150 ml portions of EtOAc. The combined organic layers were washed with saturated aqueous $NaHCO_3$ (2×150 ml), brine (1×150 ml), and dried over $Na_2SO_4$. The solution was dried under vacuum to yield an oily product which solidified gradually to yield the cream colored solid product (9.2 g, 88%). $^1$H NMR (300 MHz, $CDCl_3$): δ 0.87 (t, 3H, J=6 Hz), 1.20-1.40 (m, 10H), 1.50-1.70 (m, 2H), 3.51 (t, 2H, J=6 Hz), 6.69 (s, 2H).

N,N'-Bis(octyl)-3,9-dihydroxy-3,9-bis(phenyl)-1,2,3,7,8,9,13,14-octahydro-perylene-1,2,7,8-tetracarboxyl diimide (57)

A solution of 1,5-dibenzoyl-9,10-dihydro anthracene (55, 0.39 g, 1 mmol) and N-octyl maleimide (56, 0.465 g, 2.22 mmol) in 330 ml of benzene was vigorously degassed under $N_2$ for 45 minutes in a reactor fitted with a reflux condenser. The $N_2$ flow was reduced and the solution was stirred for 16 hours under irradiation using a 450 W medium pressure Hg lamp (Hanovia) equipped with a Pyrex filter. The solvent was removed in vacuo and the resulting crude product was triturated with $CH_3OH$ to yield the desired off-white colored products as a mixture of possible isomers (0.4 g, 49%). $^1$H NMR (300 MHz, $CDCl_3$): δ 0.40-1.30 (m, 30H), 3.08-3.15 (m, 4H), 3.65-3.70 (m, 2H), 3.90 (d, 2H, J=7.5 Hz), 4.07 (d, 2H, J=9 Hz), 5.71 (s, 2H), 7.20-7.50 (m, 14H), 7.80 (d, 2H, J=6 Hz). $^{13}$C NMR (300 MHz, $CDCl_3$): δ 14.05, 22.55, 25.83, 26.98, 28.67, 28.93, 31.78, 35.32, 38.68, 44.35, 48.14, 123.98, 126.82, 127.43, 127.77, 128.19, 128.49, 128.91, 132.12, 140.10, 141.19, 175.26, 179.80.

N,N'-Bis(octyl)-3,9-bis(phenyl)-1,7,13,14-tetrahydro-perylene-1,2,7,8-tetracarboxyl diimide (58)

A solution of the photoadduct (57, 0.5 g, 0.62 mmol) and catalytic amount of p-toluene sulfonic acid monohydrate (p-TSA) (0.11 g, 0.58 mmol) in 100 ml of toluene was refluxed for 16 hours. The resulting solution was evaporated to dryness under vacuum. Methanol (40 ml) was added to the resulting crude product and the mixture was stirred to dissolve the p-TSA. The mixture was filtered to collect the solid product, which was then used in the following aromatization step without any further purification (0.265 g, 55%). $^1$H NMR (300 MHz, $CDCl_3$): δ 0.86 (t, 6H, J=6 Hz), 1.24-1.34 (m, 20H), 1.60-1.80 (m, 4H), 3.56 (d, 2H, J=12 Hz), 3.63 (t, 4H, J=6 Hz), 4.62 (d, 2H, J=12 Hz), 7.03 (d, 2H, J=6 Hz), 7.33 (t, 2H, J=7.5 Hz), 7.40-7.60 (m, 12H). $^{13}$C NMR (300 MHz, $CDCl_3$): δ 14.00, 22.58, 27.01, 27.89, 29.11, 29.14, 31.72, 38.94, 40.62, 46.17, 124.55, 126.34, 127.85, 129.22, 129.28, 130.34, 130.99, 133.33, 133.77, 134.59, 135.95, 146.42, 166.16, 174.31.

N,N'-Bis(octyl)-3,9-bis(phenyl)-perylene-1,2,7,8-tetracarboxyl diimide (59)

A solution of the dehydrated precursor (58, 0.26 g, 0.34 mmol), sulfur (0.16 g, 5 mmol) in 6 ml of diphenylether was refluxed under $N_2$ for four hours. The solution was cooled to room temperature and 100 ml of hexanes were added. The resulting solid was collected by filtration. The solid was stirred in 100 ml of $CH_2Cl_2$ and filtered. The filtrate was concentrated in vacuo and further purified by flash column chromatography to yield the title product as an orange solid (0.17 g, 66%). $^1$H NMR (300 MHz, $CDCl_3$): δ 0.85 (t, 6H, J=6 Hz), 1.24-1.39 (m, 20H), 1.60-1.80 (m, 4H), 3.68 (t, 4H, J=6 Hz), 7.40-7.50 (m, 4H), 7.50-7.70 (m, 6H), 7.70-7.80 (m, 2H), 7.84 (d, 2H, J=9 Hz), 9.01 (d, 2H, J=9 Hz). $^{13}$C NMR (300 MHz, $CDCl_3$): δ 14.04, 22.61, 27.06, 28.44, 29.17, 31.77, 38.71, 123.35, 126.45, 128.07, 128.26, 128.33, 128.61, 129.93, 130.35, 131.90, 132.58, 133.28, 134.78, 134.92, 139.24, 166.53, 167.98. Anal. Calcd for $C_{52}H_{50}N_2O_4$: C, 81.43; H, 6.57. Found: C, 80.70; H, 6.54.

Figure 11:
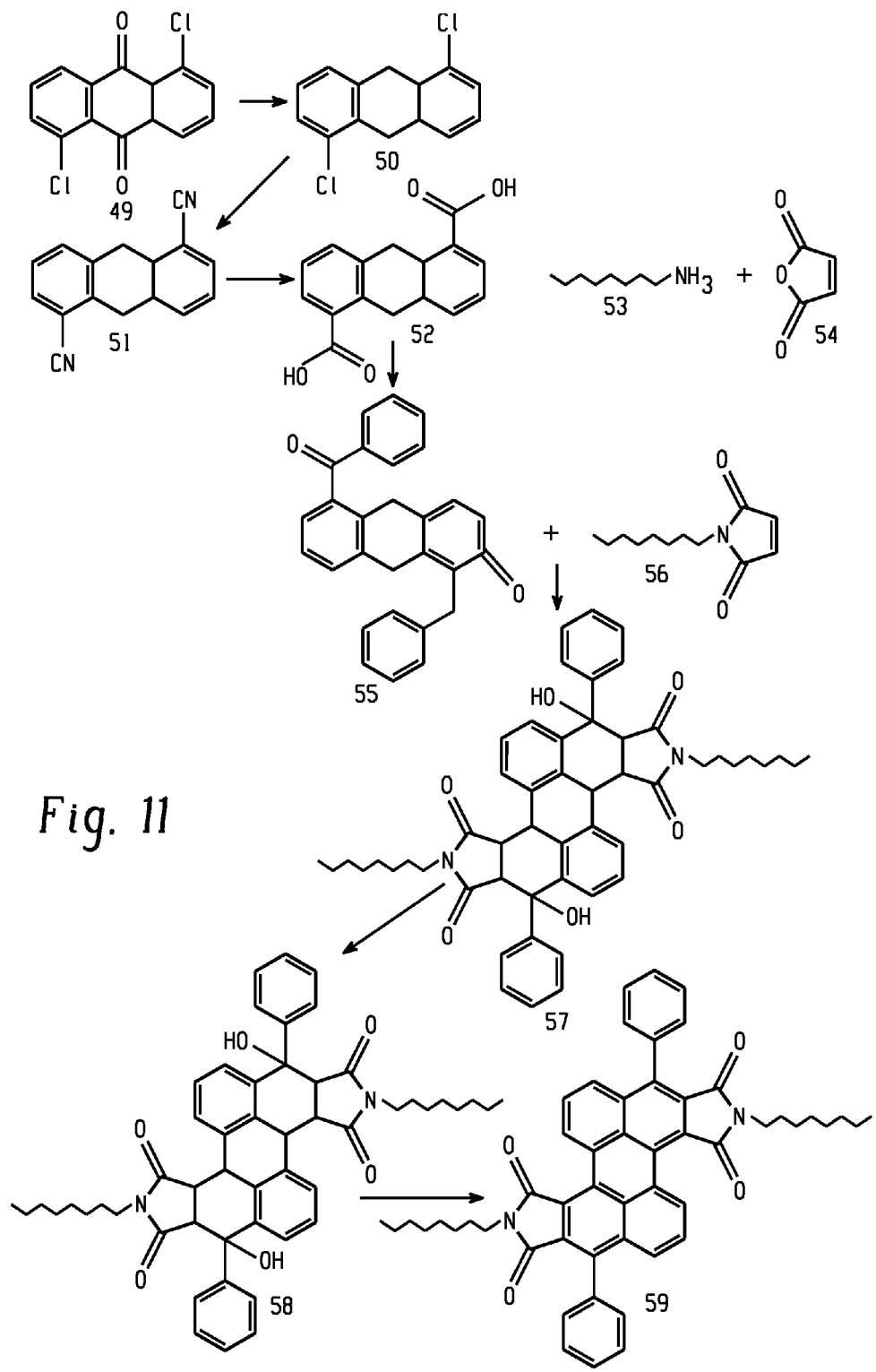
FIG. 11 shows the total synthesis of Z-Shaped perylene diimide.

This procedure describes the first synthesis of a Z-shaped perylene diimide. An overview of the procedure is provided in FIG. 11. As an important step, the Diels-Alder trapping of photochemically generated o-xylylenols was utilized. This versatile chemistry will enable the preparation of an array of new perylene diimides with various functionality on the imide rings and pendant phenyl groups.

Example 5

Absorption and Emission Behavior of Perylene Diimide

Analytically pure samples of perylene diimide (59) were used for all experiments. Purification was achieved using flash column chromatography (silica, hexane:ethyl acetate). Optimal separation was accomplished with a gradient profile; 100% hexane for 5 minutes followed by an increase of 1% per min of ethyl acetate. Samples were typically dry loaded onto the column by evaporating a concentrated solution onto a minimum amount of silica.

Unless otherwise stated, all experiments used optically dilute solutions (OD<0.2) at room temperature. Fresh samples were prepared for all measurements by dissolving the appropriate analyte in dichloromethane. Luminescence solutions were prepared under atmospheric conditions and held in anaerobic 1 cm² quartz cells (Spectracell, FUV) during interrogation. Absorption spectra were measured with a Shimadzu scanning spectrophotometer (UV-3101 PC). Emission spectra were obtained with an Aminco-Bowman luminescence spectrometer (Series 2). The excitation was accomplished with a 150 W Xe lamp optically coupled to a monochrometer (±2 nm). The emission was collected at 90° and passed through a second monochrometer (±2 μm). Luminescence was measured with a photomultiplier tube (PMT). Radiative quantum yields ($\Phi_r$) were measured against fluorescein for which $\Phi_r$=0.090 in 0.01 M NaOH, accurate to 10%, and calculated using the following equation $$\Phi_{unk} = \Phi_{std}\left(\frac{I_{unk}}{A_{unk}}\right)\left(\frac{A_{std}}{I_{std}}\right)\left(\frac{\eta_{unk}}{\eta_{std}}\right)^2$$

where unk represents the sample, std represents the standard, $\Phi$ is the radiative quantum yield, I is the integrated emission intensity, A is the absorbance at the excitation wavelength, and $\eta$ is the refractive index of the solvent.

Luminescence lifetimes were measured with an IBH time-correlated single photon counting (TCSPC) system equipped with an IBH Model TBX-04 Photon Detection Module. The excitation source for the TCSPC measurements was a pulsed LED (IBH NanoLED, 455 nm, 1.3 ns pulse duration or 403 nm, <200 ps pulse duration) with a repetition rate of 1 MHz. All data was analyzed by iterative reconvolution of the decay profile (10,000 counts at the peak channel) with the instrument response function using software provided by the instrument manufacturer.

Electrochemical measurements were recorded with an EG&G Princeton Applied Research Potentiostat/Galvanostat (Model 273A). The working electrode consisted of a platinum disk, 3 mm in diameter. A platinum mesh served as a counter electrode and a silver wire was used as a quasi reference electrode. All electrodes were polished with 0.05 μm alumina prior to measurements. Solutions were prepared with 100 mM TBAP electrolyte and degassed with argon for 20 minutes prior to each measurement. Reported potentials are versus SCE and were determined by adding ferrocene (taking $E^0_{Fc/Fc+}$=0.424 V vs SCE in benzene) as an internal potential marker.

Figure 12:
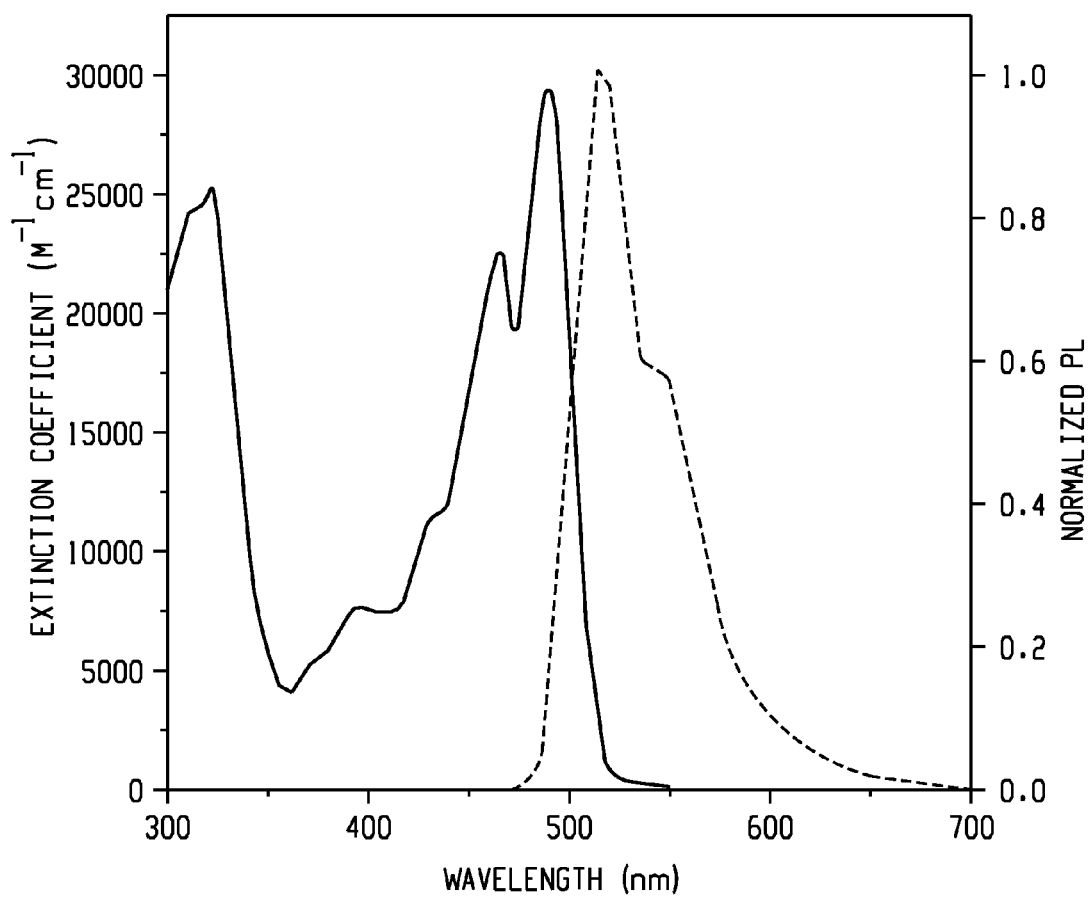
FIG. 12 shows the absorption (solid line) and normalized emission (425 nm excit.) spectra (dotted line) of Z-shaped perylene diimide in $CH_2Cl_2$.

Z-shaped perylene diimide 59 is soluble in polar organic solvents. Room temperature absorption and emission spectra of 59 are shown in FIG. 12. Compound 59 has an absorption $\lambda_{max}$ near 491 nm with an extinction coefficient of 29,000 M$^{-1}$ cm$^{-1}$. Fluorescence of 59 exhibits a Stokes' shift of 26 nm ($\lambda_{max}$=517 nm) and a quantum yield of 0.67. Intense green emission is observed both in solution and polystyrene films. Emission from 59 does not exhibit solvatochromism. Room temperature fluorescence decay measurements in CH$_2$Cl$_2$ revealed a single exponential lifetime of 5.01 ns, consistent with a singlet excited state. Solid state emission is bright orange, indicative of exciplex formation. Cyclic voltammetry on 59 in CH$_2$Cl$_2$ reveals two reversible reduction potentials at −1.08 V and −1.30 V, ca. 600 mV lower than similar linear diimides.

X-ray crystallographic analysis of single crystals of 59 revealed a substantial twist (19.5°) in the perylene core between each naphthyl unit. Previous reports have shown that highly substituted perylenes are twisted while unstrained derivatives are essentially flat. See Sadrai et al., Acta Cryst. 1990, C46, 637-40; and Klebe et al., J. Acta Cryst. 1989, B45, 69-77. Steric crowding in 59 also results in elongation (1.474 (3) Å) of the C—C bonds connecting the napthyl units indicating development of single bond character and loss of aromaticity. This data is consistent with the observed slight blue shift in the absorption and emission spectra of 59 relative to less crowded linear perylene diimides. The unit cell of 59 consists of columnar structures of perylenes alternating with n-octyl chains from the perylene diimide on an adjacent column. The observation of excimer emission from crystalline 59 is somewhat surprising given the large distance between perylenes in these columns.

These new diimides should have a broad range of applications including electron transfer systems, molecular sensors and electronics, and liquid crystalline materials.

The complete disclosures of the patents, patent documents, and publications cited herein are incorporated by reference in their entirety as if each were individually incorporated, regardless of whether they are individually incorporated by reference. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. An aromatic sensor molecule having a structure according to Formula I:

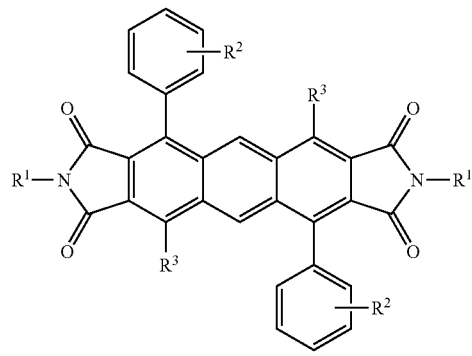

wherein R¹ is selected from the group consisting of triphenyl amines, aryl-crown ethers, porphyrins, and phenyl boronic acid, R² is selected from the group consisting of hydrogen, alkyl, haloalkyl, halogen, alkoxy, cyano, nitro, amino, alkylamino, carboxyl, and hydroxyl moieties, and R³ is selected from the group consisting of hydrogen or a phenyl group including an R² substituent.

2. An aromatic sensor molecule having a structure according to Formula II:

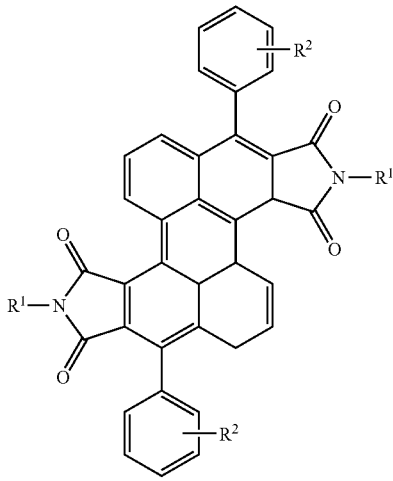

wherein R¹ is selected from the group consisting of aryl-crown ethers, aryl amines, porphyrins, and phenyl boronic acid, and R² is selected from the group consisting of hydrogen, alkyl, haloalkyl, halogen, alkoxy, cyano, nitro, amino, alkylamino, carboxyl, and hydroxyl moieties.

3. An aromatic sensor molecule having a structure according to Formula III:

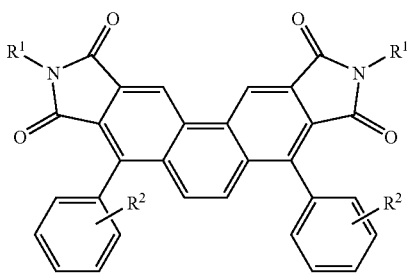

wherein R¹ is selected from the group consisting of aryl-crown ethers, aryl amines, porphyrins, and phenyl boronic acid, and R² is selected from the group consisting of hydrogen, alkyl, haloalkyl, halogen, alkoxy, cyano, nitro, amino, alkylamino, carboxyl, and hydroxyl moieties.

4. An aromatic sensor molecule having a structure according to Formula IV:

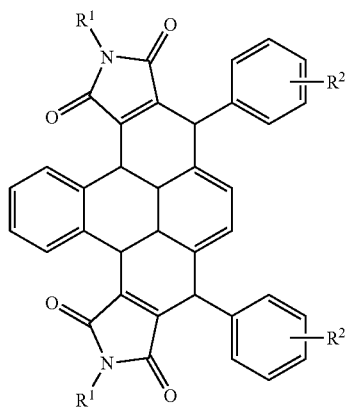

wherein R¹ is selected from the group consisting of aryl-crown ethers, aryl amines, porphyrins, and phenyl boronic acid, and R² is selected from the group consisting of hydrogen, alkyl, haloalkyl, halogen, alkoxy, cyano, nitro, amino, alkylamino, carboxyl, and hydroxyl moieties.

5. An aromatic sensor molecule having a structural formula according to Formula II:

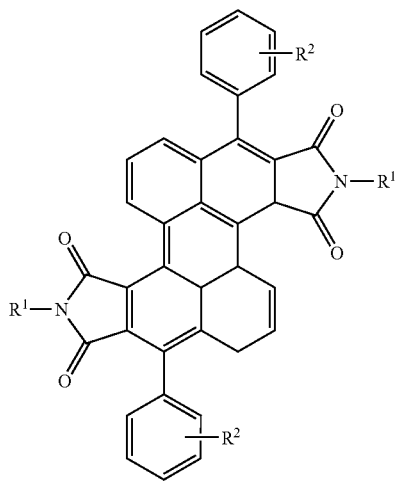

wherein R¹ is selected from the group consisting of alkyl, alkoxy, or alkoxyphenyl, and R² is selected from the group consisting of hydrogen, alkyl, haloalkyl, halogen, alkoxy, cyano, nitro, amino, alkylamino, carboxyl, and hydroxyl moieties.

6. A method of detecting molecular strain using an aromatic sensor molecule of claim 5.

7. The sensor molecule of claim 1, wherein each pendant phenyl groups, to which the $R_2$ groups are attached, is attached to a polymer.

8. The sensor molecule of claim 1, wherein each pendant phenyl groups, to which the $R_2$ groups are attached, is attached to a nanoparticle.

9. The sensor molecule of claim 1, wherein the aromatic sensor molecule exhibits peak fluorescence at a wavelength from about 450 to about 800 nanometers.

10. The sensor molecule of claim 1, wherein the aromatic sensor molecule is photostable.

11. A method of detecting a target analyte using the aromatic sensor molecule of claim 1.

12. The method of claim 11, wherein the target analyte is an acid or metal ion.

13. The method of claim 11, wherein the target analyte is a nitroaromatic explosive compound.

14. The method of claim 11, wherein the target analyte is a chemical warfare agent.

* * * * *

UNITED STATES PATENT AND TRADEMARK OFFICE
CERTIFICATE OF CORRECTION

PATENT NO.        : 8,242,162 B2
APPLICATION NO.   : 11/956848
DATED             : August 14, 2012
INVENTOR(S)       : Michael A. Meador, Daniel S. Tyson and Ulvi F. Ilan It is certified that error appears in the above-identified patent and that said Letters Patent is hereby corrected as shown below:

At Col. 16, in Scheme 1, replace "Bv" with "hv".

At Col. 17, Line 51, replace "900" with "90°".

At Col. 20, Line 56, replace "as" with "$\varepsilon_s$".

Signed and Sealed this
Twenty-third Day of October, 2012

David J. Kappos
*Director of the United States Patent and Trademark Office*